(12) United States Patent
Contorni

(10) Patent No.: US 8,765,135 B2
(45) Date of Patent: Jul. 1, 2014

(54) LIQUID VACCINES FOR MULTIPLE MENINGOCOCCAL SEROGROUPS

(75) Inventor: Mario Contorni, Siena (IT)

(73) Assignee: Novartis AG, Basel (CH)

( * ) Notice: Subject to any disclaimer, the term of this patent is extended or adjusted under 35 U.S.C. 154(b) by 1979 days.

(21) Appl. No.: 10/574,424

(22) PCT Filed: Oct. 4, 2004

(86) PCT No.: PCT/IB2004/003373
§ 371 (c)(1),
(2), (4) Date: Apr. 19, 2007

(87) PCT Pub. No.: WO2005/032583
PCT Pub. Date: Apr. 14, 2005

(65) Prior Publication Data
US 2008/0241180 A1    Oct. 2, 2008

(30) Foreign Application Priority Data

Oct. 2, 2003 (GB) .................................. 0323102.4
May 28, 2004 (GB) .................................. 0412052.3

(51) Int. Cl.
*A61K 39/00* (2006.01)
*A61K 39/02* (2006.01)
*A61K 39/095* (2006.01)
*A61K 39/116* (2006.01)

(52) U.S. Cl.
USPC .................. 424/185.1; 424/190.1; 424/203.1; 424/250.1

(58) Field of Classification Search
None
See application file for complete search history.

(56) References Cited

U.S. PATENT DOCUMENTS

| 4,879,213 | A * | 11/1989 | Fox et al. ........................... 435/5 |
| 8,007,815 | B1 | 8/2011 | Granoff et al. |
| 2003/0068336 | A1 | 4/2003 | Ryall |
| 2004/0101537 | A1* | 5/2004 | O'Hagan et al. ............ 424/249.1 |
| 2006/0008476 | A1* | 1/2006 | Pizza et al. .................. 424/250.1 |

FOREIGN PATENT DOCUMENTS

| WO | WO 99/42130 | 8/1999 |
| WO | 99/61053 A1 | 12/1999 |
| WO | 01/37863 A2 | 5/2001 |
| WO | 01/64920 A2 | 9/2001 |
| WO | WO 02/00249 | 1/2002 |
| WO | WO 02/058737 | 8/2002 |
| WO | WO 03/007985 | 1/2003 |
| WO | WO 03/020756 | 3/2003 |
| WO | WO 03/094834 | 11/2003 |
| WO | WO 2004/032958 | 4/2004 |
| WO | WO 2004/067030 | 8/2004 |
| WO | WO 2004/067033 | 8/2004 |

OTHER PUBLICATIONS

Plotkin et al (Vaccines W.B. Saunders Co. 1988, p. 571).*
Salgaller et al (Cancer Immunol. Immunother. vol. 39, pp. 105-116, 1994).*
Cripps, A. et al, "Challenges for the development of vaccines against *Haemophilus influenzae* and *Neisseria meningitidis*" Current Opinion in Inmmunology, 14 (5): 553-557 (2002).
Peltola, H. et al, "Prophylaxis of bacterial meningitis" Infectious Disease Clinics of North America, 13 (3): 685-710 (1999).
Masignani, V. et al., "Vaccination against *Neisseria meningitidis* Using Three Variants of the Lipoprotein GNA1870," J Exp. Med., 197 (6): 789-799 (2003).
Pizza, M. et al., "Identification of Vaccine Candidates Against Serogroup B Meningococcus by Whole-Genome Sequencing," Science, 287: 1816-1820 (2000).
Adu-Bobie, J. et al., "Two years in reverse vaccinology," Vaccine, 21: 605-610 (2003).
Mora, M., et al., "Reverse Vaccinology," DDT, 8 (10): 459-464 (2003).
Bröker, M., "Development of New Vaccines against Meningococcal Disease," Arzneim.-Forsch./DrugRes, 53 (12): 805-813 (2003).
Jódar, L. et al., "Development of vaccines against meningococcal disease," The Lancet, 359: 1499-1508(2002).
Lei, et al. "Quantification of Free Polysaccharide in Meningococcal Polysaccharide Diptheria Toxoid Conjugate Vaccines", Developments in Biologicals 103: 259-264 (2000).

* cited by examiner

*Primary Examiner* — Albert Navarro
(74) *Attorney, Agent, or Firm* — Helen Lee; Otis Littlefield

(57) ABSTRACT

Conjugated capsular saccharides from meningococcal serogroups C, W135 and Y are safe and immunogenic in humans when combined in a single dose. This effect is retained when a conjugated capsular saccharide from serogroup A is added. These conjugated antigens can be stably combined in a single aqueous dose without the need for lyophilisation. Broad protection against serogroup B infection can be achieved by using a small number of defined polypeptide antigens. These polypeptide antigens can be combined with the saccharide antigens without loss of protective efficacy for any of the five serogroups. Efficacy if retained even if a Hib conjugate is added. The efficacy of a serogroup W135 conjugate is enhanced by addition of protein antigens derived from a serogroup B strain. Addition of a Hib conjugate to meningococcal conjugates enhances the overall activity against meningococcus serogroup W135.

15 Claims, No Drawings

LIQUID VACCINES FOR MULTIPLE MENINGOCOCCAL SEROGROUPS

All documents cited herein are incorporated by reference in their entirety.

RELATED APPLICATIONS

This application is the U.S. National Phase of International Application No. PCT/IB2004/003373, filed Oct. 4, 2004 and published in English, which claims priority to Great Britain Application No. 0412052.3, filed May 28, 2004, and Great Britain Application No. 0323102.4, filed Oct. 2, 2003.

TECHNICAL FIELD

This invention relates to immunisation against bacterial meningitis, and particularly to combined immunisation against bacterial meningitis caused by multiple pathogens.

BACKGROUND ART

*N. meningitidis* is a non-motile, Gram-negative human pathogen that colonises the pharynx and causes meningitis (and, occasionally, septicaemia in the absence of meningitis). It causes both endemic and epidemic disease. Following the introduction of the conjugate vaccine against *Haemophilus influenzae* type B (Hib), *N. meningitidis* is the major cause of bacterial meningitis in the USA. A third pathogen responsible for bacterial meningitis is *Streptococcus pneumoniae*, but an effective vaccine (PrevNar™ [1]) is now available. Like the Hib vaccine, the pneumococcal vaccine is based on conjugated capsular saccharide antigens.

Based on the organism's capsular polysaccharide, various serogroups of *N. meningitidis* have been identified, including (A, B, C, H, I, K, L, 29E, W135, X, Y & Z. Serogroup A is the pathogen most often implicated in epidemic disease in sub-Saharan Africa. Serogroups B and C are responsible for the vast majority of cases in the United States and in most developed countries. Serogroups W135 and Y are responsible for the rest of the cases in the USA and developed countries. Although the capsular polysaccharide is an effective protective immunogen, each serogroup requires a separate saccharide antigen, and this approach is unsuitable for immunising against serogroup B. Thus the recent success with conjugated saccharide vaccines against serogroup C (Menjugate™ [2], Meningitec™ and NeisVac-C™) has had no impact disease caused by serogroups A, B, W135 or Y; on the contrary, they present a selective pressure towards the emergence of these serogroups as major causes of meningococcal disease.

An injectable tetravalent vaccine of capsular polysaccharides from serogroups A, C, Y & W135 has been known for many years [3,4] and is licensed for human use. The polysaccharides in this vaccine are unconjugated and are present at a 1:1:1:1 weight ratio [5], with 50 µg of each purified polysaccharide. Although effective in adolescents and adults, it induces a poor immune response and short duration of protection and cannot be used in infants [e.g. ref. 6]. Furthermore, the vaccines suffer from the disadvantage of requiring reconstitution from lyophilised forms at the time of use.

For serogroup B, a vaccine has proved elusive. Vaccines based on outer-membrane vesicles have been tested [e.g. ref. 7], but protection is typically restricted to the strain used to make the vaccine.

Thus there remains a need for a vaccine which protects against meningococcal serogroups A, C, W135 and Y in children, and also one which does not require reconstitution prior to administration. Furthermore, there remains a need for a vaccine which broadly protects against serogroup B.

DISCLOSURE OF THE INVENTION

The invention fulfills all of these various needs, and is based on eight separate findings. First, the inventors have found that conjugated capsular saccharides from meningococcal serogroups C, W135 and Y are safe and immunogenic in humans when combined in a single dose. Second, they have found that this effect is retained when a conjugated capsular saccharide from serogroup A is added. Third, they have found that these conjugated antigens can be stably combined in a single aqueous dose without the need for lyophilisation. Fourth, they have found that broad protection against serogroup B infection can be achieved by using a small number of defined polypeptide antigens. Fifth, they have found that these polypeptide antigens can be combined with the saccharide antigens without loss of protective efficacy for any of the five serogroups. Sixth, they have found that efficacy if retained even if a Hib conjugate is added. Seventh, they have found that the efficacy of a serogroup W135 conjugate is enhanced by addition of protein antigens derived from a serogroup B strain. Finally, they have found that addition of a Hib conjugate to meningococcal conjugates enhances the overall activity against serogroup W135 of meningococcus.

Thus the invention provides an aqueous immunogenic composition which, after administration to a subject, is able to induce an immune response that is bactericidal against serogroups B, C, W135 and Y of *N. meningitidis*, wherein the composition comprises: (i) a conjugated serogroup C capsular saccharide antigen; (ii) a conjugated serogroup W135 capsular saccharide antigen; (iii) a conjugated serogroup Y capsular saccharide antigen; and (iv) one or more polypeptide antigens from serogroup B. The aqueous composition may also induce an immune response that is bactericidal against serogroup A of *N. meningitidis*, and may thus further comprise: (v) a conjugated serogroup A capsular saccharide antigen.

The invention also provides an aqueous immunogenic composition which, after administration to a subject, is able to induce an immune response that is (a) bactericidal against at least serogroup W135 of *N. meningitidis* and (b) protective against *H. influenzae* type b disease, wherein the composition comprises: (i) a conjugated serogroup W135 capsular saccharide antigen; (ii) a conjugated *H. influenzae* type b capsular saccharide antigen. The composition may further include conjugated capsular saccharide antigens from serogroups C and Y and, optionally, A. It may further include polypeptide antigens from serogroup B of *N. meningitidis*.

Preferred saccharide antigens are oligosaccharides.

Serogroups C, W135 and Y

Techniques for preparing capsular polysaccharides from meningococci have been known for many years, and typically involve a process comprising the steps of polysaccharide precipitation (e.g. using a cationic detergent), ethanol fractionation, cold phenol extraction (to remove protein) and ultracentrifugation (to remove LPS) [e.g. see ref. 8].

A more preferred process [9] involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is particularly preferred [10]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol may be added to the precipitated polysaccharide to give a final ethanol concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration.

Once filtered to remove contaminants, the polysaccharide may be precipitated for further treatment and/or processing. This can be conveniently achieved by exchanging cations (e.g. by the addition of calcium or sodium salts).

After purification, the capsular saccharides are conjugated to carrier proteins as described below.

Further and alternative methods for purification and conjugation of meningococcal saccharides are disclosed in references 11 & 12.

As an alternative to purification, capsular saccharides of the present invention may be obtained by total or partial synthesis e.g. Hib synthesis is disclosed in ref. 13, and MenA synthesis in ref. 14.

The saccharide may be chemically modified e.g. it may be O-acetylated or de-O-acetylated. Any such de-O-acetylation or hyper-acetylation may be at specific positions in the saccharide. For instance, most serogroup C strains have O-acetyl groups at position C-7 and/or C-8 of the sialic acid residues, but about 15% of clinical isolates lack these O-acetyl groups [15,16]. The acetylation does not seem to affect protective efficacy (e.g. unlike the Menjugate™ product, the NeisVac-C™ product uses a de-O-acetylated saccharide, but both vaccines are effective). The serogroup W135 saccharide is a polymer of sialic acid-galactose disaccharide units. The serogroup Y saccharide is similar to the serogroup W135 saccharide, except that the disaccharide repeating unit includes glucose instead of galactose. Like the serogroup C saccharides, the MenW135 and MenY saccharides have variable O-acetylation, but at sialic acid 7 and 9 positions [17]. Any such chemical modifications preferably take place before conjugation, but may alternatively or additionally take place during conjugation.

Saccharides from different serogroups are preferably purified separately, and may then be combined, either before or after conjugation.

Serogroup A

Compositions of the invention may include a conjugated serogroup A capsular saccharide antigen. The saccharide can be purified and conjugated in the same way as for serogroups C, W135 and Y (see above), although it is structurally different—whereas the capsules of serogroups C, W135 and Y are based around sialic acid (N-acetyl-neuraminic acid, NeuAc), the capsule of serogroup A is based on N-acetyl-mannosamine, which is the natural precursor of sialic acid. The serogroup A saccharide is particularly susceptible to hydrolysis, and its instability in aqueous media means that (a) the immunogenicity of liquid vaccines against serogroup A declines over time, and (b) quality control is more difficult, due to release of saccharide hydrolysis products into the vaccine.

Native MenA capsular saccharide is a homopolymer of ($\alpha 1 \rightarrow 6$)-linked N-acetyl-D-mannosamine-1-phosphate, with partial O-acetylation at C3 and C4. The principal glycosidic bond is a 1-6 phosphodiester bond involving the hemiacetal group of C1 and the alcohol group of C6 of the D-mannosamine. The average chain length is 93 monomers. It has the following formula:

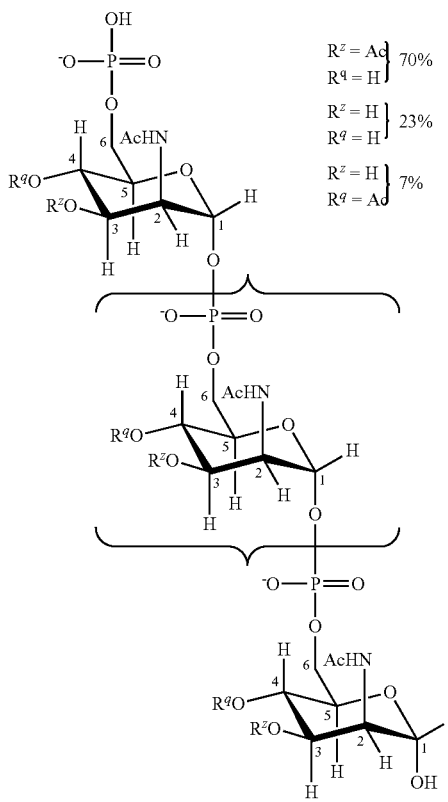

The inventors have prepared a modified saccharide antigen which retains the immunogenic activity of the native serogroup A saccharide but which is much more stable in water. Hydroxyl groups attached at carbons 3 and 4 of the monosaccharide units are replaced by a blocking group [ref. 18].

The number of monosaccharide units having blocking groups in place of hydroxyls can vary. For example, all or substantially all the monosaccharide units may have blocking groups. Alternatively, at least 10%, 20%, 30%, 40%, 50%, 60%, 70%, 80% or 90% of the monosaccharide units may have blocking groups. At least 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 monosaccharide units may have blocking groups.

Likewise, the number of blocking groups on a monosaccharide unit may vary. For example, the number of blocking groups on any particular monosaccharide unit may be 1 or 2.

The terminal monosaccharide unit may or may not have a blocking group instead of its native hydroxyl. It is preferred to retain a free anomeric hydroxyl group on a terminal monosaccharide unit in order to provide a handle for further reactions (e.g. conjugation). Anomeric hydroxyl groups can be converted to amino groups (—$NH_2$ or —NH-E, where E is a nitrogen protecting group) by reductive amination (using, for example, $NaBH_3CN/NH_4Cl$), and can then be regenerated after other hydroxyl groups have been converted to blocking groups.

Blocking groups to replace hydroxyl groups may be directly accessible via a derivatizing reaction of the hydroxyl group i.e. by replacing the hydrogen atom of the hydroxyl group with another group. Suitable derivatives of hydroxyl groups which act as blocking groups are, for example, carbamates, sulfonates, carbonates, esters, ethers (e.g. silyl ethers or alkyl ethers) and acetals. Some specific examples of such blocking groups are allyl, Aloc, benzyl, BOM, t-butyl, trityl, TBS, TBDPS, TES, TMS, TIPS, PMB, MEM, MOM, MTM, THP, etc. Other blocking groups that are not directly accessible and which completely replace the hydroxyl group include $C_{1-12}$ alkyl, $C_{3-12}$ alkyl, $C_{5-12}$ aryl, $C_{5-12}$ aryl-$C_{1-6}$ alkyl, $NR^1R^2$ ($R^1$ and $R^2$ are defined in the following paragraph), H, F, Cl, Br, $CO_2H$, $CO_2(C_{1-6}$ alkyl), CN, $CF_3$, $CCl_3$, etc.

Preferred blocking groups are of the formula: —O—X—Y or —$OR^3$ wherein: X is C(O), S(O) or $SO_2$; Y is $C_{1-12}$ alkyl, $C_{1-12}$ alkoxy, $C_{3-12}$ cycloalkyl, $C_{5-12}$ aryl or $C_{5-12}$ aryl-$C_{1-6}$ alkyl, each of which may optionally be substituted with 1, 2 or 3 groups independently selected from F, Cl, Br, $CO_2H$, $CO_2$ ($C_{1-6}$ alkyl), CN, $CF_3$ or $CCl_3$; or Y is $NR^1R^2$; $R^1$ and $R^2$ are independently selected from H, $C_{1-12}$ alkyl, $C_{3-12}$ cycloalkyl, $C_{5-12}$ aryl, $C_{5-12}$ aryl-$C_{1-6}$ alkyl; or $R^1$ and $R^2$ may be joined to form a $C_{3-12}$ saturated heterocyclic group; $R^3$ is $C_{1-12}$ alkyl or $C_{3-12}$ cycloalkyl, each of which may optionally be substituted with 1, 2 or 3 groups independently selected from F, Cl, Br, $CO_2(C_{1-6}$ alkyl), CN, $CF_3$ or $CCl_3$; or $R^3$ is $C_{5-12}$ aryl or $C_{5-12}$ aryl-$C_{1-6}$ alkyl, each of which may optionally be substituted with 1, 2, 3, 4 or 5 groups selected from F, Cl, Br, $CO_2H$, $CO_2(C_{1-6}$ alkyl), CN, $CF_3$ or $CCl_3$. When $R^3$ is $C_{1-12}$ alkyl or $C_{3-12}$ cycloalkyl, it is typically substituted with 1, 2 or 3 groups as defined above. When $R^1$ and $R^2$ are joined to form a $C_{3-12}$ saturated heterocyclic group, it is meant that $R^1$ and $R^2$ together with the nitrogen atom form a saturated heterocyclic group containing any number of carbon atoms between 3 and 12 (e.g. $C_3$, $C_4$, $C_5$, $C_6$, $C_7$, $C_8$, $C_9$, $C_{10}$, $C_{11}$, $C_{12}$). The heterocyclic group may contain 1 or 2 heteroatoms (such as N, O or S) other than the nitrogen atom. Examples of $C_{3-12}$ saturated heterocyclic groups are pyrrolidinyl, piperidinyl, morpholinyl, piperazinyl, imidazolidinyl, azetidinyl and aziridinyl.

Blocking groups —O—X—Y and —$OR^3$ can be prepared from —OH groups by standard derivatizing procedures, such as reaction of the hydroxyl group with an acyl halide, alkyl halide, sulfonyl halide, etc. Hence, the oxygen atom in —O—X—Y is preferably the oxygen atom of the hydroxyl group, while the —X—Y group in —O—X—Y preferably replaces the hydrogen atom of the hydroxyl group.

Alternatively, the blocking groups may be accessible via a substitution reaction, such as a Mitsonobu-type substitution. These and other methods of preparing blocking groups from hydroxyl groups are well known.

More preferably, the blocking group is —$OC(O)CF_3$ [19], or a carbamate group —$OC(O)NR^1R^2$, where $R^1$ and $R^2$ are independently selected from $C_{1-6}$ alkyl. More preferably, $R^1$ and $R^2$ are both methyl i.e. the blocking group is —$OC(O)NMe_2$. Carbamate blocking groups have a stabilizing effect on the glycosidic bond and may be prepared under mild conditions.

Preferred modified MenA saccharides contain n monosaccharide units, where at least h % of the monosaccharide units do not have —OH groups at both of positions 3 and 4. The value of h is 24 or more (e.g. 25, 26, 27, 28, 29, 30, 35, 40, 45, 50, 55, 60, 65, 70, 75, 80, 85, 90, 95, 98, 99 or 100) and is preferably 50 or more. The absent —OH groups are preferably blocking groups as defined above.

Other preferred modified MenA saccharides comprise monosaccharide units, wherein at least s of the monosaccharide units do not have —OH at the 3 position and do not have —OH at the 4 position. The value of s is at least 1 (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90). The absent —OH groups are preferably blocking groups as defined above.

Suitable modified MenA saccharides for use with the invention have the formula:

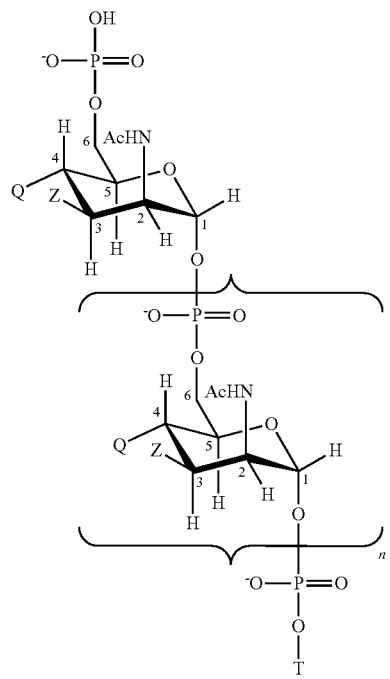

wherein
n is an integer from 1 to 100 (preferably an integer from 5 to 25, more preferably 15-25);
T is of the formula (A) or (B):

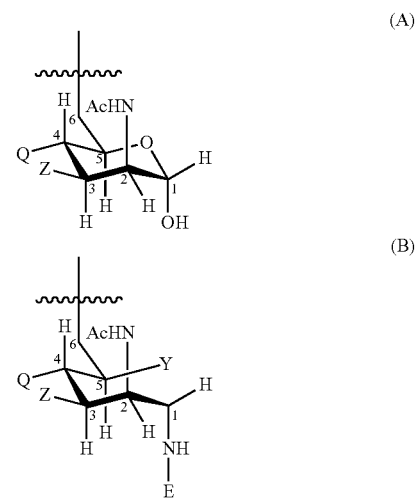

each Z group is independently selected from OH or a blocking group as defined above; and
each Q group is independently selected from OH or a blocking group as defined above;
Y is selected from OH or a blocking group as defined above;
E is H or a nitrogen protecting group;
and wherein more than about 7% (e.g. 8%, 9%, 10% or more) of the Q groups are blocking groups.

Each of the n+2 Z groups may be the same or different from each other. Likewise, each of the n+2 Q groups may be the same or different from each other. All the Z groups may be OH. Alternatively, at least 10%, 20, 30%, 40%, 50% or 60% of the Z groups may be OAc. Preferably, about 70% of the Z groups are OAc, with the remainder of the Z groups being OH or blocking groups as defined above. At least about 7% of Q groups are blocking groups. Preferably, at least 10%, 20%, 30%, 40%, 50%, 60%, 70%, 80%, 90% or even 100% of the Q groups are blocking groups.

Preferred blocking groups are electron-withdrawing groups. Without wishing to be bound by theory, it is believed that glycosidic bonds are unstable to hydrolysis due to assistance from an intramolecular nucleophilic attack of a saccharide hydroxyl group on the glycosidic linkage (i.e. by formation of a cyclic intermediate). The greater the nucleophilicity of the hydroxyl group, the greater the tendency for intramolecular nucleophilic attack. An electron-withdrawing blocking group has the effect of delocalizing the oxygen lone pair, thereby decreasing the oxygen nucleophilicity and decreasing the tendency for intramolecular nucleophilic attack.

For protecting against serogroup A, therefore, the aqueous compositions can include a MenA modified saccharide as defined above.

Preferred compositions of the invention can be stored for 28 days at 37° C. and, after that period, less than f % of the initial total amount of conjugated MenA saccharide will be unconjugated, where f is 20, 19, 18, 17, 16, 15, 14, 13, 12, 11, 10, 9, 8, 7, 6, 5 or lower.

Covalent Conjugation

Capsular saccharides in compositions of the invention will usually be conjugated to carrier protein(s). In general, conjugation enhances the immunogenicity of saccharides as it converts them from T-independent antigens to T-dependent antigens, thus allowing priming for immunological memory. Conjugation is particularly useful for paediatric vaccines and is a well known technique [e.g. reviewed in refs. 20 to 29].

Preferred carrier proteins are bacterial toxins or toxoids, such as diphtheria toxoid or tetanus toxoid, or the CRM$_{197}$ diphtheria toxin mutant [30-32]. Other suitable carrier proteins include the *N. meningitidis* outer membrane protein [33], synthetic peptides [34,35], heat shock proteins [36,37], *pertussis* proteins [38,39], cytokines [40], lymphokines [40], hormones [40], growth factors [40], artificial proteins comprising multiple human CD4$^+$ T cell epitopes from various pathogen-derived antigens [41] such as the N19 protein [42], protein D from *H. influenzae* [43,44], pneumolysin [45], pneumococcal surface protein PspA [46], iron-uptake proteins [47], toxin A or B from *C. difficile* [48], mutant bacterial toxins (e.g. cholera toxin 'CT' or *E. coli* heat labile toxin 'LT'), such as a CT with a substitution at Glu-29 [49], etc. Preferred carriers are diphtheria toxoid, tetanus toxoid, *H. influenzae* protein D, and particularly CRM$_{197}$.

Within a composition of the invention, it is possible to use more than one carrier protein e.g. to reduce the risk of carrier suppression. Thus different carrier proteins can be used for different serogroups e.g. serogroup A saccharides might be conjugated to CRM$_{197}$ while serogroup C saccharides might be conjugated to tetanus toxoid. It is also possible to use more than one carrier protein for a particular saccharide antigen e.g. serogroup A saccharides might be in two groups, with some conjugated to CRM$_{197}$ and others conjugated to tetanus toxoid. In general, however, it is preferred to use the same carrier protein for all serogroups, with CRM$_{197}$ being the preferred choice.

A single carrier protein might carry more than one saccharide antigen [50]. For example, a single carrier protein might have conjugated to it saccharides from serogroups A and C. To achieve this goal, saccharides can be mixed prior to the conjugation reaction. In general, however, it is preferred to have separate conjugates for each serogroup.

Conjugates with a saccharide:protein ratio (w/w) of between 1:5 (i.e. excess protein) and 5:1 (i.e. excess saccharide) are preferred. Ratios between 1:2 and 5:1 are preferred, as are ratios between 1:1.25 and 1:2.5 are more preferred. Excess carrier protein may be preferred for MenA and MenC.

Conjugates may be used in conjunction with free carrier protein [51]. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [52, 53, etc.]). Other suitable techniques use carbodiimides, hydrazides, active esters, norborane, p-nitrobenzoic acid, N-hydroxysuccinimide, S—NHS, EDC, TSTU; see also the introduction to reference 27).

Linkages via a linker group may be made using any known procedure, for example, the procedures described in references 54 and 55. One type of linkage involves reductive amination of the polysaccharide, coupling the resulting amino group with one end of an adipic acid linker group, and then coupling a protein to the other end of the adipic acid linker group [25,56,57]. Other linkers include B-propionamido [58], nitrophenyl-ethylamine [59], haloacyl halides [60], glycosidic linkages [61], 6-aminocaproic acid [62], ADH [63], $C_4$ to $C_{12}$ moieties [64] etc. As an alternative to using a linker, direct linkage can be used. Direct linkages to the protein may comprise oxidation of the polysaccharide followed by reductive amination with the protein, as described in, for example, references 65 and 66.

A process involving the introduction of amino groups into the saccharide (e.g. by replacing terminal =O groups with —NH$_2$) followed by derivatisation with an adipic diester (e.g. adipic acid N-hydroxysuccinimido diester) and reaction with carrier protein is preferred. Another preferred reaction uses CDAP activation with a protein D carrier e.g. for MenA or MenC.

After conjugation, free and conjugated saccharides can be separated. There are many suitable methods, including hydrophobic chromatography, tangential ultrafiltration, diafiltration, etc. [see also refs. 67 & 68, etc.].

Where the composition of the invention includes a conjugated oligosaccharide, it is preferred that oligosaccharide preparation precedes conjugation.

After conjugation, methods of the invention may include a step of measuring the level of unconjugated carrier protein. One way of making this measurement involves capillary electrophoresis [69] (e.g. in free solution), or micellar electrokinetic chromatography [70].

After conjugation, methods of the invention may include a step of measuring the level of unconjugated saccharide. One way of making this measurement involves HPAEC-PAD [67].

After conjugation, methods of the invention may include a step of separating conjugated saccharide from unconjugated saccharide. One way of separating these saccharides is to use a method that selectively precipitates one component. Selective precipitation of conjugated saccharide is preferred, to leave unconjugated saccharide in solution, e.g. by a deoxycholate treatment [67].

After conjugation, methods of the invention may include a step of measuring the molecular size and/or molar mass of a conjugate. In particular, distributions may be measured. One way of making these measurements involves size exclusion chromatography with detection by multiangle light scattering photometry and differential refractometry (SEC-MALS/RI) [71].

Oligosaccharides

Capsular saccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of less than 30 (e.g. between 10 and 20, preferably around 10 for serogroup A; between 15 and 25 for serogroups W135 and Y, preferably around 15-20; between 12 and 22 for serogroup C; etc.). DP can conveniently be measured by ion exchange chromatography or by colorimetric assays [72].

If hydrolysis is performed, the hydrolysate will generally be sized in order to remove short-length oligosaccharides [73]. This can be achieved in various ways, such as ultrafiltration followed by ion-exchange chromatography. Oligosaccharides with a degree of polymerisation of less than or equal to about 6 are preferably removed for serogroup A, and those less than around 4 are preferably removed for serogroups W135 and Y.

Chemical hydrolysis of saccharides generally involves treatment with either acid or base under conditions that are standard in the art. Conditions for depolymerisation of capsular saccharides to their constituent monosaccharides are known in the art. One depolymerisation method involves the use of hydrogen peroxide [11]. Hydrogen peroxide is added to a saccharide (e.g. to give a final $H_2O_2$ concentration of 1%), and the mixture is then incubated (e.g. at around 55° C.) until a desired chain length reduction has been achieved. The reduction over time can be followed by removing samples from the mixture and then measuring the (average) molecular size of saccharide in the sample. Depolymerization can then be stopped by rapid cooling once a desired chain length has been reached.

Serogroup B

Vaccines against pathogens such as hepatitis B virus, diphtheria and tetanus typically contain a single protein antigen (e.g. the HBV surface antigen, or a tetanus toxoid). In contrast, acellular whooping cough vaccines typically contain at least three *B. pertussis* proteins and the PrevNar™ pneumococcal vaccine contains seven separate conjugated saccharide antigens. Other vaccines such as cellular *pertussis* vaccines, the measles vaccine, the inactivated polio vaccine (IPV) and meningococcal OMV vaccines are by their very nature complex mixtures of a large number of antigens. Whether protection against can be elicited by a single antigen, a small number of defined antigens, or a complex mixture of undefined antigens, therefore depends on the pathogen in question.

As mentioned above, a vaccine against serogroup B meningococcus has proved elusive. OMV-based vaccines show narrow efficacy. Moreover, the large number of undefined antigens present in an OMV, combined with their variable nature, means that OMVs have various quality control problems.

The inventors have found that broad protection against serogroup B infection can be achieved, and that this can be achieved by using a small number of defined serogroup B polypeptide antigens, and so the compositions of the invention include one or more polypeptide antigens such that the composition can induce an immune response that is bactericidal against two or more (i.e. 2 or 3) of hypervirulent lineages A4, ET-5 and lineage 3 of *N. meningitidis* serogroup B.

Genome sequences for meningococcal serogroups A [74] and B [75,76] have been reported, and suitable antigens can be selected from the encoded polypeptides [e.g. refs. 77-82]. Candidate antigens have been manipulated to improve heterologous expression [refs. 83 to 85].

One preferred composition includes a Tbp protein and a Hsf protein [86]. Hsf is an autotransporter protein [87-89], also known as nhhA [89], GNA0992 [77] or NMB0992 [75]. Tbp is the transferrin binding protein [90-93], and encompasses both TbpA and TbpB and the high molecular weight and low molecular weight forms of TbpA and TbpB. Tbp encompasses individual proteins described above and complexes of the proteins and any other proteins or complexes thereof capable of binding transferrin. Although Tbp can refer to either the high or low molecular forms of TbpA or TbpB, it is preferred that both high molecular weight and low molecular weight forms of TbpA and/or TbpB are present. Most preferably, high molecular weight and low molecular weight TbpA is present.

Another preferred composition includes serogroup B lipooligosaccharide (LOS) [94]. LOS can be used in addition to the serogroup B polypeptide(s) or can be used in place of it/them.

Another preferred composition includes at least one antigen selected from each of at least two different categories of protein having different functions within *Neisseria*. Examples of such categories of proteins are: adhesins, autotransporter proteins, toxins, integral outer membrane proteins and iron acquisition proteins. These antigens may be selected as follows, using the nomenclature of reference 95: at least one Neisserial adhesin selected from the group consisting of FhaB, NspA PilC, Hsf, Hap, MafA, MafB, Omp26, NMB0315, NMB0995, NMB1119 and NadA; at least one Neisserial autotransporter selected from the group consisting of Hsf, Hap, IgA protease, AspA, and NadA; at least one Neisserial toxin selected from the group consisting of FrpA, FrpC, FrpA/C, VapD, NM-ADPRT (NMB1343) and either or both of LPS immunotype L2 and LPS immunotype L3; at least one Neisserial Fe acquisition protein selected from the group consisting of TbpA, TbpB, LbpA, LbpB, HpuA, HpuB, Lipo28 (GNA2132), Sibp, NMB0964, NMB0293, FbpA, Bcp, BfrA, BfrB and P2086 (XthA); at least one Neisserial membrane-associated protein, preferably outer membrane protein, particularly integral outer membrane protein, selected from the group consisting of PilQ, OMP85, FhaC, NspA, TbpA, LbpA, TspA, TspB, TdfH, PorB, MltA, HpuB, HimD, HisD, GNA1870, OstA, HlpA (GNA1946), NMB1124, NMB1162, NMB1220, NMB1313, NMB1953, HtrA, and PLDA (OMPLA). These combinations of Neisserial antigens are said to lead to a surprising enhancement of the efficacy of the vaccine against Neisserial infection [95].

Particularly preferred compositions include one or more of the following five antigens [96]: (1) a 'NadA' protein, preferably in oligomeric form (e.g. in trimeric form); (2) a '741' protein; (3) a '936' protein; (4) a '953' protein; and (5) a '287' protein.

'NadA' (Neisserial adhesin A) from MenB is disclosed as protein '961' in reference 80 (SEQ IDs 2943 & 2944) and as 'NMB1994' in reference 75 (see also GenBank accession numbers: 11352904 & 7227256). A detailed study of the protein can be found in reference 97. When used according to the present invention, NadA may take various forms. Preferred forms of NadA are truncation or deletion variants, such as those disclosed in references 83 to 85. In particular, NadA without its C-terminal membrane anchor is preferred (e.g. deletion of residues 351-405 for the 2996 strain, to give SEQ ID NO:1 herein), which is sometimes distinguished herein by the use of a 'C' superscript e.g. NadA$^{(C)}$. Expression of NadA without its membrane anchor domain in *E. coli* results in secretion of the protein into the culture supernatant with concomitant removal of its 23mer leader peptide (e.g. to leave a 327mer for strain 2996 [SEQ ID NO:2 herein]). Polypeptides without their leader peptides are sometimes distinguished herein by the use of a 'NL' superscript e.g. NadA$^{(NL)}$ or NadA$^{(C)(NL)}$. Preferred NadA polypeptides have an amino acid sequence which: (a) has 50% or more identity (e.g. 60%, 70%, 80%, 90%, 95%, 99% or more) to SEQ ID NO:2; and/or (b) comprises a fragment of at least n consecutive amino acids of SEQ ID NO:1, wherein n is 7 or more (eg. 8, 10, 12, 14, 16, 18, 20, 25, 30, 35, 40, 50, 60, 70, 80, 90, 100, 150, 200, 250 or more). Preferred fragments for (b) lack one or more amino acids (e.g. 1, 2, 3, 4, 5, 6, 7, 8, 9, 10, 15, 20, 25 or more) from the C-terminus and/or the N-terminus of SEQ ID NO:1 (e.g. NadA$^{(C)}$, NadA$^{(NL)}$, NadA$^{(C)(NL)}$). Other preferred fragments comprise an epitope from SEQ ID 1, and a particularly preferred fragment of SEQ ID 1 is SEQ ID 2. These various sequences includes NadA variants (e.g. allelic variants, homologs, orthologs, paralogs, mutants, etc.). Various NadA sequences are shown in FIG. 9 of reference 98.

'741' protein from MenB is disclosed in reference 80 (SEQ IDs 2535 & 2536) and as 'NMB1870' in reference 75 (see also GenBank accession number GI:7227128). The corresponding protein in serogroup A [74] has GenBank accession number 7379322. 741 is naturally a lipoprotein. When used according to the present invention, 741 protein may take various forms. Preferred forms of 741 are truncation or deletion variants, such as those disclosed in references 83 to 85. In particular, the N-terminus of 741 may be deleted up to and including its poly-glycine sequence (i.e. deletion of residues 1 to 72 for strain MC58 [SEQ ID NO:3 herein]), which is sometimes distinguished herein by the use of a 'ΔG' prefix. This deletion can enhance expression. The deletion also removes 741's lipidation site. Preferred 741 sequences have an amino acid sequence which: (a) has 50% or more identity (e.g. 60%, 70%, 80%, 90%, 95%, 99% or more) to SEQ ID NO:3; and/or (b) comprises a fragment of at least n consecutive amino acids from SEQ ID NO:3, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from 741. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:3. These sequences include 741 variants (e.g. allelic variants, homologs, orthologs, paralogs, mutants, etc.). Various 741 sequences can be found in SEQ IDs 1 to 22 of reference 85, in SEQ IDs 1 to 23 of reference 99, and in SEQ IDs 1-299 of reference 100.

'936' protein from serogroup B is disclosed in reference 80 (SEQ IDs 2883 & 2884) and as 'NMB2091' in reference 75 (see also GenBank accession number GI:7227353). The corresponding gene in serogroup A [74] has GenBank accession number 7379093. When used according to the present invention, 936 protein may take various forms. Preferred forms of 936 are truncation or deletion variants, such as those disclosed in references 83 to 85. In particular, the N-terminus leader peptide of 936 may be deleted (e.g. deletion of residues 1 to 23 for strain MC58, to give 936$^{(NL)}$ [SEQ ID NO:4 herein]). Preferred 936 sequences have an amino acid sequence which: (a) has 50% or more identity (e.g. 60%, 70%, 80%, 90%, 95%, 99% or more) to SEQ ID NO:4; and/or (b) comprises a fragment of at least n consecutive amino acids from SEQ ID NO:4, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from 936. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:4. These sequences include 936 variants (e.g. allelic variants, homologs, orthologs, paralogs, mutants, etc.).

'953' protein from serogroup B is disclosed in reference 80 (SEQ IDs 2917 & 2918) and as 'NMB1030' in reference 75 (see also GenBank accession number GI:7226269). The corresponding protein in serogroup A [74] has GenBank accession number 7380108. When used according to the present invention, 953 protein may take various forms. Preferred forms of 953 are truncation or deletion variants, such as those disclosed in references 83 to 85. In particular, the N-terminus leader peptide of 953 may be deleted (e.g. deletion of residues 1 to 19 for strain MC58, to give 953$^{(NL)}$ [SEQ ID NO:5 herein]. Preferred 953 sequences have an amino acid sequence which: (a) has 50% or more identity (e.g. 60%, 70%, 80%, 90%, 95%, 99% or more) to SEQ ID NO:5; and/or (b) comprises a fragment of at least n consecutive amino acids from SEQ ID NO:5, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from 953. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:5. These sequences include 936 variants (e.g allelic variants, homologs, orthologs, paralogs, mutants, etc.). Allelic forms of 953 can be seen in FIG. 19 of reference 82.

'287' protein from serogroup B is disclosed in reference 80 (SEQ IDs 3103 & 3104), as 'NMB2132' in reference 75, and as 'GNA2132' in reference 77 (see also GenBank accession number GI:7227388). The corresponding protein in serogroup A [74] has GenBank accession number 7379057. When used according to the present invention, 287 protein may take various forms. Preferred forms of 287 are truncation or deletion variants, such as those disclosed in references 83 to 85. In particular, the N-terminus of 287 may be deleted up to and including its poly-glycine sequence (e.g. deletion of residues 1 to 24 for strain MC58, to give ΔG287 [SEQ ID NO:6 herein]. This deletion can enhance expression. Preferred 287 sequences have an amino acid sequence which: (a) has 50% or more identity (e.g. 60%, 70%, 80%, 90%, 95%, 99% or more) to SEQ ID NO:6; and/or (b) comprises a fragment of at least n consecutive amino acids from SEQ ID NO:6, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from 287. Other preferred fragments lack one or more amino acids (e.g. 1, 2, 3, 4, 5, 6, 7, 8, 9, 10, 15, 20, 25 or more) from the C-terminus and/or the N-terminus of SEQ ID NO:6. These sequences include 287 variants (e.g allelic variants, homologs, orthologs, paralogs, mutants, etc.). Allelic forms of 287 can be seen in FIGS. 5 and 15 of reference 82, and in example 13 and FIG. 21 of reference 80 (SEQ IDs 3179 to 3184).

Preferred MenB antigens comprise an amino acid sequence found in one of strains are 2996, MC58, 95N477, and 394/98. Protein 287 is preferably from strain 2996 or, more preferably, from strain 394/98. Protein 741 is preferably from serogroup B strains MC58, 2996, 394/98, or 95N477, or from serogroup C strain 90/18311. Strain MC58 is more preferred. Proteins 936, 953 and NadA are preferably from strain 2996. Where a composition includes a particular protein antigen (e.g. 741 or 287), the composition can include that antigen in more than one variant form e.g. the same protein, but from more than one strain. These proteins may be included as tandem or separate proteins.

In some embodiments, however, the composition of the invention includes the same protein but from more than one strain. This approach has been found to be effective with the 741 protein. This protein is an extremely effective antigen for eliciting anti-meningococcal antibody responses, and it is expressed across all meningococcal serogroups. Phylogenetic analysis shows that the protein splits into two groups, and that one of these splits again to give three variants in total [101], and while serum raised against a given variant is bactericidal within the same variant group, it is not active against strains which express one of the other two variants i.e. there is intra-variant cross-protection, but not inter-variant cross-protection [99,101]. For maximum cross-strain efficacy, therefore, it is preferred that a composition should include more than one variant of protein 741. An exemplary sequence from each variant is given in SEQ ID NOS: 10, 11 and 12 herein, starting with a N-terminal cysteine residue to which lipid will be covalently attached in the native lipoprotein form. It is therefore preferred that the composition should include at least two of: (1) a first protein, comprising an amino acid sequence having at least a % sequence identity to SEQ ID NO:10 and/or comprising an amino acid sequence consisting of a fragment of at least x contiguous amino acids from SEQ ID NO:10; (2) a second protein, comprising an amino acid sequence having at least b % sequence identity to SEQ ID NO:11 and/or comprising an amino acid sequence consisting of a fragment of at least y contiguous amino acids from SEQ ID NO:11; and (3) a third protein, comprising an amino acid sequence having at least c % sequence identity to SEQ ID NO:12 and/or comprising an amino acid sequence consisting of a fragment of at least z contiguous amino acids from SEQ ID NO:12. The value of a is at least 85 e.g. 86, 87, 88, 89, 90, 91, 92, 93, 94, 95, 96, 97, 98, 99, 99.5, or more. The value of b is at least 85 e.g. 86, 87, 88, 89, 90, 91, 92, 93, 94, 95, 96, 97, 98, 99, 99.5, or more. The value of c is at least 85 e.g. 86, 87, 88, 89, 90, 91, 92, 93, 94, 95, 96, 97, 98, 99, 99.5, or more. The values of a, b and c are not intrinsically related to each other. The value of x is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of y is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The value of z is at least 7 e.g. 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 225, 250). The values of x, y and z are not intrinsically related to each other. It is preferred that any given 741 amino acid sequence will not fall into more than one of categories (1), (2) and (3). Any given 741 sequence will thus fall into only one of categories (1), (2) and (3). It is thus preferred that: protein (1) has less than i % sequence identity to protein (2); protein (1) has less than j % sequence identity to protein (3); and protein (2) has less than k % sequence identity to protein (3). The value of i is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most a. The value of j is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most b. The value of k is 60 or more (e.g. 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, etc.) and is at most c. The values of i, j and k are not intrinsically related to each other.

Compositions of the invention include a small number (e.g. fewer than t antigens, where t is 10, 9, 8, 7, 6, 5, 4 or 3) of purified serogroup B antigens. It is particularly preferred that the composition should not include complex or undefined mixtures of antigens e.g. it is preferred not to include outer membrane vesicles in the composition. The antigens are preferably expressed recombinantly in a heterologous host and then purified. For a composition including t MenB antigens, there may be t separate polypeptides but, to reduce complexity even further, it is preferred that at least two of the antigens are expressed as a single polypeptide chain (a 'hybrid' protein [refs. 83 to 85]) i.e. such that the t antigens form fewer than t polypeptides. Hybrid proteins offer two principal advantages: first, a protein that may be unstable or poorly expressed on its own can be assisted by adding a suitable hybrid partner that overcomes the problem; second, commercial manufacture is simplified as only one expression and purification need be employed in order to produce two separately-useful proteins. A hybrid protein included in a composition of the invention may comprise two or more (i.e. 2, 3, 4 or 5) of the five antigens listed above. Hybrids consisting of two of the five antigens are preferred.

Within the combination of five basic antigens (NadA, 741, 953, 936 & 287), an antigen may be present in more than one hybrid protein and/or as a non-hybrid protein. It is preferred, however, that an antigen is present either as a hybrid or as a non-hybrid, but not as both, although it may be useful to include protein 741 both as a hybrid and a non-hybrid (preferably lipoprotein) antigen, particularly where more than one variant of 741 is used.

Hybrid proteins can be represented by the formula $NH_2$-A-[-X-L-]$_n$—B—COOH, wherein: X is an amino acid sequence of one of the five basic antigens; L is an optional linker amino acid sequence; A is an optional N-terminal amino acid sequence; B is an optional C-terminal amino acid sequence; and n is 2, 3, 4 or 5.

Most preferably, n is 2. Two-antigen hybrids for use in the invention comprise: NadA & 741; NadA & 936; NadA & 953; NadA & 287; 741 & 936; 741 & 953; 741 & 287; 936 & 953; 936 & 287; 953 & 287. Two preferred proteins are: $X_1$ is a 936 and $X_2$ is a 741; $X_1$ is a 287 and $X_2$ is a 953.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2$ ... $X_n$ will be omitted. This is equivalent to deleting all leader peptides and using the leader peptide of $X_1$ as moiety -A-.

For each n instances of [—X-L-], linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. A useful linker is GSGGGG (SEQ ID 9), with the Gly-Ser dipeptide being formed from a BamHI restriction site, thus aiding cloning and manipulation, and the (Gly)$_4$ tetrapeptide being a typical poly-glycine linker. If $X_{n+1}$ is a ΔG protein and $L_n$ is a glycine linker, this may be equivalent to $X_{n+1}$ not being a ΔG protein and $L_n$ being absent.

-A- is an optional N-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more), or sequences which enhance protein stability. Other suitable C-terminal amino acid sequences will be apparent to those skilled in the art.

Two particularly preferred hybrid proteins of the invention are as follows:

| n | A | $X_1$ | $L_1$ | $X_2$ | $L_2$ | B | SEQ ID NO: |
|---|---|---|---|---|---|---|---|
| 2 | MA | ΔG287 | GSGGGG | 953$^{(NL)}$ | — | — | 7 |
| 2 | M | 936$^{(NL)}$ | GSGGGG | ΔG741 | — | — | 8 |

These two proteins may be used in combination with NadA (particularly with SEQ ID NO:2). Thus a preferred composition of MenB antigens for use with the invention thus includes a first polypeptide comprising amino acid sequence SEQ ID NO:2, a second polypeptide comprising amino acid sequence SEQ ID NO:7 and a third polypeptide comprising amino acid sequence SEQ ID NO:8. This is a preferred group of MenB antigens for use with the invention.

As mentioned above, compositions of the invention can induce a serum bactericidal antibody response that is effective against two or three of MenB hypervirulent lineages A4, ET-5 and lineage 3. They may additionally induce bactericidal antibody responses against one or more of hypervirulent lineages subgroup I, subgroup III, subgroup IV-1 or ET-37 complex, and against other lineages e.g. hyperinvasive lineages. These antibody responses are conveniently measured in mice and are a standard indicator of vaccine efficacy [e.g. see end-note 14 of reference 77]. Serum bactericidal activity (SBA) measures bacterial killing mediated by complement, and can be assayed using human or baby rabbit complement. WHO standards require a vaccine to induce at least a 4-fold rise in SBA in more than 90% of recipients.

The composition need not induce bactericidal antibodies against each and every MenB strain within these hypervirulent lineages; rather, for any given group of four of more strains of serogroup B meningococcus within a particular hypervirulent lineage, the antibodies induced by the composition are bactericidal against at least 50% (e.g. 60%, 70%, 80%, 90% or more) of the group. Preferred groups of strains will include strains isolated in at least four of the following countries: GB, AU, CA, NO, IT, US, NZ, NL, BR, and CU. The serum preferably has a bactericidal titre of at least 1024 (e.g. $2^{10}$, $2^{11}$, $2^{12}$, $2^{13}$, $2^{14}$, $2^{15}$, $2^{16}$, $2^{17}$, $2^{18}$ or higher, preferably at least $2^{14}$) i.e. the serum is able to kill at least 50% of test bacteria of a particular strain when diluted 1/1024, as described in reference 77.

Preferred compositions can induce bactericidal responses against the following strains of serogroup B meningococcus: (i) from cluster A4, strain 961-5945 (B:2b:P1.21,16) and/or strain G2136 (B:−); (ii) from ET-5 complex, strain MC58 (B:15:P1.7,16b) and/or strain 44/76 (B:15:P1.7,16); (iii) from lineage 3, strain 394/98 (B:4:P1.4) and/or strain BZ198 (13:NT:−). More preferred compositions can induce bactericidal responses against strains 961-5945, 44/76 and 394/98. Strains 961-5945 and G2136 are both *Neisseria* MLST reference strains [ids 638 & 1002 in ref. 102]. Strain MC58 is widely available (e.g. ATCC BAA-335) and was the strain sequenced in reference 75. Strain 44/76 has been widely used and characterised (e.g. ref. 103) and is one of the *Neisseria* MLST reference strains [id 237 in ref. 102; row 32 of Table 2 in ref. 104]. Strain 394/98 was originally isolated in New Zealand in 1998, and there have been several published studies using this strain (e.g. refs. 105 & 106). Strain BZ198 is another MLST reference strain [id 409 in ref. 102; row 41 of Table 2 in ref. 104]. The composition may additionally induce a bactericidal response against serogroup W135 strain LNP17592 (W135:2a:P1.5,2), from ET-37 complex. This is a Haji strain isolated in France in 2000.

Other MenB polypeptide antigens which may be included in compositions of the invention include those comprising one of the following amino acid sequences: SEQ ID NO:650 from ref. 78; SEQ ID NO:878 from ref. 78; SEQ ID NO:884 from ref. 78; SEQ ID NO:4 from ref. 79; SEQ ID NO:598 from ref. 80; SEQ ID NO:818 from ref. 80; SEQ ID NO:864 from ref. 80; SEQ ID NO:866 from ref. 80; SEQ ID NO:1196 from ref. 80; SEQ ID NO:1272 from ref. 80; SEQ ID NO:1274 from ref. 80; SEQ ID NO:1640 from ref. 80; SEQ ID NO:1788 from ref. 80; SEQ ID NO:2288 from ref. 80; SEQ ID NO:2466 from ref. 80; SEQ ID NO:2554 from ref. 80; SEQ ID NO:2576 from ref. 80; SEQ ID NO:2606 from ref. 80; SEQ ID NO:2608 from ref. 80; SEQ ID NO:2616 from ref. 80; SEQ ID NO:2668 from ref. 80; SEQ ID NO:2780 from ref. 80; SEQ ID NO:2932 from ref. 80; SEQ ID NO:2958 from ref. 80; SEQ ID NO:2970 from ref. 80; SEQ ID NO:2988 from ref. 80, or a polypeptide comprising an amino acid sequence which: (a) has 50% or more identity (e.g. 60%, 70%, 80%, 90%, 95%, 99% or more) to said sequences; and/or (b) comprises a fragment of at least n consecutive amino acids from said sequences, wherein n is 7 or more (eg. 8, 10, 12, 14, 16, 18, 20, 25, 30, 35, 40, 50, 60, 70, 80, 90, 100, 150, 200, 250 or more). Preferred fragments for (b) comprise an epitope from the relevant sequence. More than one (e.g. 2, 3, 4, 5, 6, 7, 8, 9, 10, 11, 12, 13, 14 or more) of these polypeptides may be included.

Further Antigenic Components

Non-meningococcal and non-neisserial antigens, preferably ones that do not diminish the immune response against the meningococcal components, may also be included in compositions of the invention. Ref. 107, for instance, discloses combinations of oligosaccharides from *N. meningitidis* serogroups B and C together with the Hib saccharide. Particularly preferred non-meningococcal antigens include:

a diphtheria antigen, such as a diphtheria toxoid [e.g. chapter 3 of ref. 108].

a tetanus antigen, such as a tetanus toxoid [e.g. chapter 4 of ref. 108].

*pertussis* holotoxin (PT) and filamentous haemagglutinin (FHA) from *B. pertussis*, optionally also in combination with pertactin and/or agglutinogens 2 and 3 [e.g. refs. 109 & 110].

cellular *pertussis* antigen.

an antigen from hepatitis A virus, such as inactivated virus [e.g. 111, 112].

an antigen from hepatitis B virus, such as the surface and/or core antigens [e.g. 112,113], with surface antigen preferably being adsorbed onto an aluminium phosphate [114].

polio antigen(s) [e.g. 115, 116] such as IPV.

The mixture may comprise one or more of these further antigens, which may be detoxified where necessary (e.g. detoxification of *pertussis* toxin by chemical and/or genetic means).

Where a diphtheria antigen is included in the mixture it is preferred also to include tetanus antigen and *pertussis* antigens. Similarly, where a tetanus antigen is included it is preferred also to include diphtheria and *pertussis* antigens. Similarly, where a *pertussis* antigen is included it is preferred also to include diphtheria and tetanus antigens.

Antigens in the mixture will typically be present at a concentration of at least 1 µg/ml each. In general, the concentration of any given antigen will be sufficient to elicit an immune response against that antigen. It is preferred that the protective efficacy of individual saccharide antigens is not removed by combining them, although actual immunogenicity (e.g. ELISA titres) may be reduced.

As an alternative to using proteins antigens in the mixture, nucleic acid encoding the antigen may be used. Protein components of the mixture may thus be replaced by nucleic acid (preferably DNA e.g. in the form of a plasmid) that encodes the protein. Similarly, compositions of the invention may comprise proteins which mimic saccharide antigens e.g. mimotopes [117] or anti-idiotype antibodies. These may replace individual saccharide components, or may supplement them. As an example, the vaccine may comprise a peptide mimic of the MenC [118] or the MenA [119] capsular polysaccharide in place of the saccharide itself.

Two preferred non-meningococcal antigens for inclusion in compositions of the invention are those which protect against *H. influenzae* type B (Hib) and against *Streptococcus pneumoniae*.

*Haemophilus influenzae* Type B (Hib)

Where the composition includes a *H. influenzae* type B antigen, it will typically be a Hib capsular saccharide antigen. Saccharide antigens from *H. influenzae* b are well known.

Advantageously, the Hib saccharide is covalently conjugated to a carrier protein, in order to enhance its immunogenicity, especially in children. The preparation of polysaccharide conjugates in general, and of the Hib capsular polysaccharide in particular, is well documented [e.g. references 21-29, etc.]. The invention may use any suitable Hib conjugate. Suitable carrier proteins are described above, and preferred carriers for Hib saccharides are $CRM_{197}$ ('HbOC'), tetanus toxoid ('PRP-T') and the outer membrane complex of *N. meningitidis* ('PRP-OMP').

The saccharide moiety of the conjugate may be a polysaccharide (e.g. full-length polyribosylribitol phosphate (PRP)), but it is preferred to hydrolyse polysaccharides to form oligosaccharides (e.g. MW from ~1 to ~5 kDa).

A preferred conjugate comprises a Hib oligosaccharide covalently linked to $CRM_{197}$ via an adipic acid linker [120, 121]. Tetanus toxoid is also a preferred carrier.

Administration of the Hib antigen preferably results in an anti-PRP antibody concentration of ≥0.15 µg/ml, and more preferably ≥1 µg/ml.

Where a composition includes a Hib saccharide antigen, it is preferred that it does not also include an aluminium hydroxide adjuvant. If the composition includes an aluminium phosphate adjuvant then the Hib antigen may be adsorbed to the adjuvant [122] or it may be non-adsorbed [123]. Prevention of adsorption can be achieved by selecting the correct pH during antigen/adjuvant mixing, an adjuvant with an appropriate point of zero charge, and an appropriate order of mixing for the various different antigens in a composition [124].

Compositions of the invention may comprise more than one Hib antigen. Hib antigens may be lyophilised e.g. for reconstitution by meningococcal compositions of the invention.

*Streptococcus pneumoniae*

Where the composition includes a *S. pneumoniae* antigen, it will typically be a capsular saccharide antigen which is preferably conjugated to a carrier protein [e.g. refs. 125 to 127]. It is preferred to include saccharides from more than one serotype of *S. pneumoniae*. For example, mixtures of polysaccharides from 23 different serotype are widely used, as are conjugate vaccines with polysaccharides from between 5 and 11 different serotypes [128]. For example, PrevNar™ [1] contains antigens from seven serotypes (4, 6B, 9V, 14, 18C, 19F, and 23F) with each saccharide individually conjugated to $CRM_{197}$ by reductive amination, with 2 µg of each saccharide per 0.5 ml dose (4 µg of serotype 6B), and with conjugates adsorbed on an aluminium phosphate adjuvant. Compositions of the invention preferably include at least serotypes 6B, 14, 19F and 23F. Conjugates may be adsorbed onto an aluminium phosphate.

As an alternative to using saccharide antigens from pneumococcus, the composition may include one or more polypeptide antigens. Genome sequences for several strains of pneumococcus are available [129,130] and can be subjected to reverse vaccinology [131-134] to identify suitable polypeptide antigens [135,136]. For example, the composition may include one or more of the following antigens: PhtA, PhtD, PhtB, PhtE, SpsA, LytB, LytC, LytA, Sp125, Sp101, Sp128, Sp130 and Sp130, as defined in reference 137. The composition may include more than one (e.g. 2, 3, 4, 5, 6, 7, 8, 9 10, 11, 12, 13 or 14) of these antigens.

In some embodiments, the composition may include both saccharide and polypeptide antigens from pneumococcus. These may be used in simple admixture, or the pneumococcal saccharide antigen may be conjugated to a pneumococcal protein. Suitable carrier proteins for such embodiments include the antigens listed in the previous paragraph [137].

Pneumococcal antigens may be lyophilised e.g. together with Hib antigen.

Pharmaceutical Compositions

The composition of the invention will typically, in addition to the components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [138], trehalose [139], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 140.

Compositions of the invention are in aqueous form i.e. solutions or suspensions. Liquid formulation of this type allows the compositions to be administered direct from their packaged form, without the need for reconstitution in an aqueous medium, and are thus ideal for injection. Compositions may be presented in vials, or they may be presented in ready-filled syringes. The syringes may be supplied with or without needles. A syringe will include a single dose of the composition, whereas a vial may include a single dose or multiple doses.

Liquid compositions of the invention are also suitable for reconstituting other vaccines from a lyophilised form e.g. to reconstitute lyophilised Hib or DTP antigens. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of 0.5 ml.

The pH of the composition is preferably between 6 and 8, preferably about 7. Stable pH may be maintained by the use of a buffer. If a composition comprises an aluminium hydroxide salt, it is preferred to use a histidine buffer [141]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Within each dose, the quantity of an individual saccharide antigen will generally be between 1-50 µg (measured as mass of saccharide) e.g. about 1 µg, about 2.5 µg, about 4 µg, about 5 µg, or about 10 µg.

Each saccharide may be present at substantially the same quantity per dose. However, the ratio (w/w) of MenY saccharide:MenW135 saccharide may be greater than 1 (e.g. 2:1, 3:1, 4:1, 5:1, 10:1 or higher) and/or the ratio (w/w) of MenY saccharide:MenC saccharide may be less than 1 (e.g. 1:2, 1:3, 1:4, 1:5, or lower).

Preferred ratios (w/w) for saccharides from serogroups A:C:W135:Y are: 1:1:1:1; 1:1:1:2; 2:1:1:1; 4:2:1:1; 8:4:2:1; 4:2:1:2; 8:4:1:2; 4:2:2:1; 2:2:1:1; 4:4:2:1; 2:2:1:2; 4:4:1:2; and 2:2:2:1. Preferred ratios (w/w) for saccharides from serogroups C:W135:Y are: 1:1:1; 1:1:2; 1:1:1; 2:1:1; 4:2:1; 2:1:2; 4:1:2; 2:2:1; and 2:1:1. Using a substantially equal mass of each saccharide is preferred.

Preferred compositions of the invention comprise less than 50 µg meningococcal saccharide per dose. Other preferred compositions comprise ≤40 µg meningococcal saccharide per dose. Other preferred compositions comprise ≤30 µg meningococcal saccharide per dose. Other preferred compositions comprise ≤25 µg meningococcal saccharide per dose. Other preferred compositions comprise ≤20 µg meningococcal saccharide per dose. Other preferred compositions comprise ≤10 µg meningococcal saccharide per dose but, ideally, compositions of the invention comprise at least 10 µg total meningococcal saccharide per dose.

Compositions of the invention may include an antimicrobial, particularly when packaged in multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention will generally be administered in conjunction with other immunoregulatory agents. In particular, compositions will usually include one or more adjuvants. Such adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 142], or mixtures of different mineral compounds, with the compounds taking any suitable form (e.g. gel, crystalline, amorphous, etc.), and with adsorption being preferred. The mineral containing compositions may also be formulated as a particle of metal salt [143].

B. Oil Emulsions

Oil emulsion compositions suitable for use as adjuvants in the invention include squalene-water emulsions, such as MF59 [Chapter 10 of ref. 142; see also ref. 144] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref. 142]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 145. Saponin formulations may also comprise a sterol, such as cholesterol [146].

Combinations of saponins and cholesterols can be used to form unique particles called immunostimulating complexes (ISCOMs) [chapter 23 of ref. 142]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 146-148. Optionally, the ISCOMS may be devoid of additional detergent [149].

A review of the development of saponin based adjuvants can be found in refs. 150 & 151.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 152-157. Virosomes are discussed further in, for example, ref. 158

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 159. Such "small particles" of 3dMPL are small enough to be sterile filtered through a 0.22 μm membrane [159]. Other non-toxic LPS derivatives include monophosphoryl lipid A mimics, such as aminoalkyl glucosaminide phosphate derivatives e.g. RC-529 [160,161].

Lipid A derivatives include derivatives of lipid A from *Escherichia coli* such as OM-174. OM-174 is described for example in refs. 162 & 163.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 164, 165 and 166 disclose possible analog substitutions e.g. replacement of guanosine with 2'-deoxy-7-deazaguanosine. The adjuvant effect of CpG oligonucleotides is further discussed in refs. 167-172.

The CpG sequence may be directed to TLR9, such as the motif GTCGTT or TTCGTT [173]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 174-176. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 173 & 177-179.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or *pertussis* ("PT"). The use of detoxified ADP-ribosylating toxins as mucosal adjuvants is described in ref. 180 and as parenteral adjuvants in ref. 181. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 182-189. Numerical reference for amino acid substitutions is preferably based on the alignments of the A and B subunits of ADP-ribosylating toxins set forth in ref. 190, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [191], etc.) [192], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [193] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [194].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 142)

Examples of liposome formulations suitable for use as adjuvants are described in refs. 195-197.

J. Polyoxyethylene Ether and Polyoxyethylene Ester Formulations

Adjuvants suitable for use in the invention include polyoxyethylene ethers and polyoxyethylene esters [198]. Such formulations further include polyoxyethylene sorbitan ester surfactants in combination with an octoxynol [199] as well as polyoxyethylene alkyl ethers or ester surfactants in combination with at least one additional non-ionic surfactant such as an octoxynol [200]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 201 and 202.

L. Muramyl Peptides

Examples of muramyl peptides suitable for use as adjuvants in the invention include N-acetylmuramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 203 and 204.

The invention may also comprise combinations of aspects of one or more of the adjuvants identified above. For example, the following adjuvant compositions may be used in the invention: (1) a saponin and an oil-in-water emulsion [205]; (2) a saponin (e.g. QS21)+a non-toxic LPS derivative (e.g. 3dMPL) [206]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [207]; (5) combinations of 3dMPL with, for example, QS21 and/or oil-in-water emulsions [208]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 142.

The use of aluminium salt adjuvants is particularly preferred, and antigens are generally adsorbed to such salts. The Menjugate™ and NeisVac™ MenC conjugates use a hydroxide adjuvant, whereas Meningitec™ uses a phosphate. It is possible in compositions of the invention to adsorb some antigens to an aluminium hydroxide but to have other antigens in association with an aluminium phosphate. In general, however, it is preferred to use only a single salt e.g. a hydroxide or a phosphate, but not both. Aluminium hydroxide is preferably avoided as an adjuvant, particularly if the composition includes a Hib antigen. Compositions that do not contain aluminium hydroxide are thus preferred. Rather, aluminium phosphates may be used, and a typical adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

Not all conjugates need to be adsorbed i.e. some or all can be free in solution.

Calcium phosphate is another preferred adjuvant.

Methods of Treatment

The invention also provides a method for raising an antibody response in a mammal, comprising administering a pharmaceutical composition of the invention to the mammal.

The invention provides a method for raising an immune response in a mammal comprising the step of administering an effective amount of a composition of the invention. The immune response is preferably protective and preferably involves antibodies. The method may raise a booster response.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides a composition of the invention for use as a medicament. The medicament is preferably able to raise an immune response in a mammal (i.e. it is an immunogenic composition) and is more preferably a vaccine.

The invention also provides the use of a (i) a conjugated serogroup C capsular saccharide antigen; (ii) a conjugated serogroup W135 capsular saccharide antigen; (iii) a conjugated serogroup Y capsular saccharide antigen; (iv) one or more polypeptide antigens from serogroup B; and, optionally, (v) a conjugated serogroup A capsular saccharide antigen, in the manufacture of a medicament for raising an immune response in a mammal.

These uses and methods are preferably for the prevention and/or treatment of a disease caused by a *Neisseria* (e.g. meningitis, septicaemia, bacteremia, gonorrhoea, etc.). The prevention and/or treatment of bacterial and/or meningococcal meningitis is preferred.

One way of checking efficacy of therapeutic treatment involves monitoring Neisserial infection after administration of the composition of the invention. One way of checking efficacy of prophylactic treatment involves monitoring immune responses against the five basic antigens after administration of the composition. Immunogenicity of compositions of the invention can be determined by administering them to test subjects (e.g. children 12-16 months age, or animal models [209]) and then determining standard parameters including serum bactericidal antibodies (SBA) and ELISA titres (GMT) of total and high-avidity anti-capsule IgG. These immune responses will generally be determined around 4 weeks after administration of the composition, and compared to values determined before administration of the composition. A SBA increase of at least 4-fold or 8-fold is preferred. Where more than one dose of the composition is administered, more than one post-administration determination may be made.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Neisserial infections affect various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 210 & 211]. Success with nasal administration of pneumococcal saccharides [212,213], pneumococcal polypeptides [214], Hib saccharides [215], MenC saccharides [216], and mixtures of Hib and MenC saccharide conjugates [217] has been reported.

Storage Stability

The compositions of the invention offer improved stability, particularly for the serogroup A saccharide component. The invention provides a process for preparing a vaccine composition, comprising the steps of: (1) mixing (i) a conjugated serogroup C capsular saccharide antigen, (ii) a conjugated serogroup W135 capsular saccharide antigen, (iii) a conjugated serogroup Y capsular saccharide antigen, and (iv) one or more polypeptide antigens from serogroup B; (2) storing the composition resulting from step (1) for at least 1 week; (3) preparing a syringe containing the stored composition from step (2), ready for injection to a patient; and, optionally (4) injecting the composition into the patient.

Step (1) may also involve mixing (v) a conjugated serogroup A capsular saccharide antigen. It may also involve mixing (vi) a conjugated Hib antigen. It may also involve mixing (vii) a pneumococcal antigen. Step (2) preferably involves at least 2 weeks, 4 weeks, 6 weeks, 8 weeks, 10 weeks, 12 weeks or longer of storage. Storage step (2) may or may not be below room temperature (e.g. at 10±10° C.).

The invention also provides a process for preparing a vaccine composition, comprising the steps of: (1) mixing (i) a conjugated serogroup C capsular saccharide antigen, (ii) a conjugated serogroup W135 capsular saccharide antigen, (iii) a conjugated serogroup Y capsular saccharide antigen, and (iv) one or more polypeptide antigens from serogroup B; and (2) extracting a unit dose volume from the mixed antigens; and (c) packaging the extracted unit dose in a hermetically-sealed container.

Step (1) may also involve mixing (v) a conjugated serogroup A capsular saccharide antigen. It may also involve mixing (vi) a conjugated Hib antigen. It may also involve mixing (vii) a pneumococcal antigen. The hermetically-sealed container may be a vial or a syringe.

The invention provides a hermetically-sealed container, containing a composition of the invention.

General

The term "comprising" means "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 218. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 219.

The term "alkyl" refers to alkyl groups in both straight and branched forms, The alkyl group may be interrupted with 1, 2 or 3 heteroatoms selected from —O—, —NH— or —S—. The alkyl group may also be interrupted with 1, 2 or 3 double and/or triple bonds. However, the term "alkyl" usually refers to alkyl groups having no heteroatom interruptions or double or triple bond interruptions. Where reference is made to $C_{1-12}$ alkyl, it is meant the alkyl group may contain any number of carbon atoms between 1 and 12 (e.g. $C_1, C_2, C_3, C_4, C_5, C_6, C_7, C_8, C_9, C_{10}, C_{11}, C_{12}$). Similarly, where reference is made to $C_{1-6}$ alkyl, it is meant the alkyl group may contain any number of carbon atoms between 1 and 6 (e.g. $C_1, C_2, C_3, C_4, C_5, C_6$).

The term "cycloalkyl" includes cycloalkyl, polycycloalkyl, and cycloalkenyl groups, as well as combinations of these with alkyl groups, such as cycloalkylalkyl groups. The cycloalkyl group may be interrupted with 1, 2 or 3 heteroatoms selected from —O—, —NH— or —S—. However, the term "cycloalkyl" usually refers to cycloalkyl groups having no heteroatom interruptions Examples of cycloalkyl groups include cyclopentyl, cyclohexyl, cyclohexenyl, cyclohexylmethyl and adamantyl groups. Where reference is made to $C_{3-12}$ cycloalkyl, it is meant that the cycloalkyl group may contain any number of carbon atoms between 3 and 12 (e.g. $C_3, C_4, C_5, C_6, C_7, C_8, C_9, C_{10}, C_{11}, C_{12}$).

The term "aryl" refers to an aromatic group, such as phenyl or naphthyl. Where reference is made to $C_{5-12}$ aryl, it is meant that the aryl group may contain any number of carbon atoms between 5 and 12 (e.g. $C_5, C_6, C_7, C_8, C_9, C_{10}, C_{11}, C_{12}$).

The term "$C_{5-12}$ aryl-$C_{1-6}$ alkyl" refers to groups such as benzyl, phenylethyl and naphthylmethyl.

Nitrogen protecting groups include silyl groups (such as TMS, TES, TBS, TIPS), acyl derivatives (such as phthalimides, trifluoroacetamides, methoxycarbonyl, ethoxycarbonyl, t-butoxycarbonyl (Boc), benzyloxycarbonyl (Z or Cbz), 9-fluorenylmethoxycarbonyl (Fmoc), 2-(trimethylsilyl) ethoxy carbonyl, 2,2,2-trichloroethoxycarbonyl (Troc)), sulfonyl derivatives (such as β-trimethylsilylethanesulfonyl (SES)), sulfenyl derivatives, $C_{1-12}$ alkyl, benzyl, benzhydryl, trityl, 9-phenylfluorenyl etc. A preferred nitrogen protecting group is Fmoc.

Sequences included to facilitate cloning or purification, etc., do not necessarily contribute to the invention and may be omitted or removed.

It will be appreciated that sugar rings can exist in open and closed form and that, whilst closed forms are shown in structural formulae herein, open forms are also encompassed by the invention.

Polypeptides of the invention can be prepared by various means (e.g. recombinant expression, purification from cell culture, chemical synthesis (at least in part), etc.) and in various forms (e.g. native, fusions, non-glycosylated, lipidated, etc.). They are preferably prepared in substantially pure form (i.e. substantially free from other *N. meningitidis* or host cell proteins). Whilst expression of the polypeptide may take place in *Neisseria*, a heterologous host is preferred. The heterologous host may be prokaryotic (e.g. a bacterium) or eukaryotic. It is preferably *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeast, etc.

Nucleic acid according to the invention can be prepared in many ways (e.g. by chemical synthesis (at least in part), from genomic or cDNA libraries, from the organism itself, etc.) and can take various forms (e.g. single stranded, double stranded, vectors, probes, etc.). They are preferably prepared in substantially pure form (i.e. substantially free from other *N. meningitidis* or host cell nucleic acids). The term "nucleic acid" includes DNA and RNA, and also their analogues, such as those containing modified backbones (e.g. phosphorothioates, etc.), and also peptide nucleic acids (PNA) etc. The invention includes nucleic acid comprising sequences complementary to those described above (eg. for antisense or probing purposes).

After serogroup, meningococcal classification includes serotype, serosubtype and then immunotype, and the standard nomenclature lists serogroup, serotype, serosubtype, and immunotype, each separated by a colon e.g. B:4:P1.15:L3,7, 9. Within serogroup B, some lineages cause disease often (hyperinvasive), some lineages cause more severe forms of disease than others (hypervirulent), and others rarely cause disease at all. Seven hypervirulent lineages are recognised, namely subgroups I, III and IV-1, ET-5 complex, ET-37 complex, A4 cluster and lineage 3. These have been defined by multilocus enzyme electrophoresis (MLEE), but multilocus sequence typing (MLST) has also been used to classify meningococci [ref. 104].

MODES FOR CARRYING OUT THE INVENTION

ΔG287-953 Hybrid Protein

DNA encoding protein 287 from meningococcal serogroup B strain 394/98 and protein 953 from meningococcal serogroup B strain 2996 were digested and ligated, together with a short linker sequence, to give a plasmid encoding amino acid sequence SEQ ID 7. The plasmid was transfected into *E. coli* and bacteria were grown to express the protein. After adequate growth, bacteria were harvested and the protein was purified. From culture, bacteria were centrifuged and the pellet was homogenized in the presence of 50 mM acetate buffer (pH 5) with a pellet:buffer volume ratio of 1:8. Lysis was performed using a high pressure homogenizer (AVESTIN, 4 cycles at 14000 psi). After lysis, urea was added at final concentration of 5M, followed by agitation for 1 hour at room temperature. The pH was reduced from 6 to 5 using 200 mM acetate buffer (pH 4)+5 M urea. The mixture was centrifuged at 16800 g for 60 minutes at 2-8° C. The supernatant was collected and filtered by SARTOBRAN P (0.45-0.22 μm SARTORIUS). Protein in the filtered supernatant was stable for at least 30 days at −20° C. and for at least 15 days at 2-8° C.

Protein was further purified on a cationic exchange column (SPFF, Amersham Biosciences) with elution using 350 mM NaCl+50 mM acetate+5 M urea pH 5.00. The majority of impurities were present in the flow-thru. A pre-elution washing using a lower NaCl concentration (180 mM) advantageously eliminated two contaminating *E. coli* proteins.

The eluted material was adjusted to pH 8 (using 200 mM TRIS/HCl+5 M urea pH 9) and further purified on a Q Sepharose HP column (Amersham) with elution using 150 mM NaCl+20 mM TRIS/HCl pH 8.00 in 5 M urea. Again, a pre-elution washing with reduced salt (90 mM) was useful for eliminating impurities.

The filtered eluted material from Q HP column was diluted 1:2 using PBS pH 7.00 (150 mM NaCl+10 mM potassium phosphate, pH 7.00) and then diafiltered against 10 volumes of PBS pH 7.00 by tangential ultrafiltration. At the end of diafiltration the material was concentrated 1.6 times to about 1.2 mg/ml total proteins. Using a 30,000 Da cut-off membrane (Regenerated Cellulose membrane 50 $cm^2$, Millipore PLCTK 30) it was possible to dialyze the material with a yield of about 90%.

936-ΔG741 Hybrid Protein

DNA encoding protein 936 from meningococcal serogroup B strain 2996 and protein 741 from meningococcal serogroup B strain MC58 were digested and ligated, together with a short linker sequence, to give a plasmid encoding amino acid sequence SEQ ID 8. The plasmid was transfected into *E. coli* and bacteria were grown to express the protein. The recombinant protein was not secreted, but remained soluble within the bacteria.

After adequate growth, bacteria were centrifuged to give a humid paste and treated as follows:

- Homogenisation by high pressure system in presence of 20 mM sodium phosphate pH 7.00.
- Centrifugation and clarification by orthogonal filtration.
- Cationic column chromatography (SP Sepharose Fast Flow), with elution by 150 mM NaCl in 20 mM sodium phosphate pH 7.00.
- Anionic column chromatography (Q Sepharose XL) with flow-through harvesting.
- Hydrophobic column chromatography (Phenyl Sepharose 6 Fast Flow High Sub) with elution by 20 mM sodium phosphate, pH 7.00.
- Diafiltration against PBS pH 7.4 with a 1 Kd cut-off.
- Final sterile filtration and storing at −20° C.

Protein in the final material was stable for at least 3 months both at −20° C. and at 2-8° C.

$NadA^{(NL)(C)}$ Protein

DNA encoding NadA protein from meningococcal serogroup B strain 2996 was digested to remove the sequence encoding its C-terminus, to give a plasmid encoding amino acid sequence SEQ ID 1. The plasmid was transfected into *E. coli* and bacteria were grown to express the protein. The recombinant protein was secreted into the culture medium, and the leader peptide was absent in the secreted protein (SEQ ID 2). The supernatant was treated as follows:

- Concentration 7× and diafiltration against buffer 20 mM TRIS/HCl pH7.6 by cross flow UF (Cut off 30 Kd).
- Anionic column chromatography (Q Sepharose XL), with elution by 400 mM NaCl in 20 mM TRIS/HCl pH 7.6.
- Hydrophobic column chromatography step (Phenyl Sepharose 6 Fast Flow High Sub), with elution by 50 mM NaCl in TRIS/HCl pH 7.6.
- Hydroxylapatite ceramic column chromatography (HA Macro. Prep) with elution by 200 mM sodium phosphate pH 7.4.
- Diafiltration (cut off 30 Kd) against PBS pH 7.4
- Final sterile filtration and storing at −20° C.

Protein in the final material was stable for at least 6 months both at −20° C. and at 2-8° C.

NadA protein is susceptible to degradation, and truncated forms of NadA may be detected by western blot or by mass spectrometry (e.g. by MALDI-TOF) indicating up to 10 kDa MW loss. Degradation products can be separated from native NadA by gel filtration (e.g. using column TSK 300SWXL, precolumn TSKSWXL, TOSOHAAS). Such filtration gives three peaks: (i) a first peak with retention time 12.637 min and apparent MW 885.036 Da; (ii) retention time 13.871 min and apparent MW 530.388 Da; (iii) retention time 13.871 min and apparent MW 530.388 Da. Light scattering analysis of the three peaks reveals real MW values of (i) 208500 Da, (ii) 98460 Da, (iii) 78760 Da. Thus the first peak contains NadA aggregates, and the third peak contains degradation products.

As the predicted molecular weight of $NadA^{(NL)(C)}$ is 34.113 Da, peak (ii) contains a trimeric protein, which is the desired antigen.

Antigenic Combinations

Mice were immunised with a composition comprising the three proteins and, for comparison purposes, the three proteins were also tested singly. Ten mice were used per group. The mixture was able to induce high bactericidal titres against various strains:

| Meningococcal strain(Serogroup) | | | | | | | |
|---|---|---|---|---|---|---|---|
| 2996(B) | MC58(B) | NGH38 | 394/98(B) | H44/76(B) | F6124(A) | BZ133(C) | C11(C) |
| (1) 32000 | 16000 | 130000 | 16000 | 32000 | 8000 | 16000 | 8000 |
| (2) 256 | 131000 | 128 | 16000 | 32000 | 8000 | 16000 | <4 |
| (3) 32000 | 8000 | — | — | — | 8000 | — | 32000 |
| Mix 32000 | 32000 | 65000 | 16000 | 260000 | 65000 | >65000 | 8000 |

'—' indicates that this strain contains no NadA gene

Looking at individual mice, the triple mixture induced high and consistent bactericidal titres against the three serogroup B strains from which the individual antigens are derived:

| | # | | | | | | | | | |
|---|---|---|---|---|---|---|---|---|---|---|
| | 1 | 2 | 3 | 4 | 5 | 6 | 7 | 8 | 9 | 10 |
| 2996 | 32768 | 16384 | 65536 | 32768 | 32768 | 65536 | 65536 | 32768 | 65536 | 8192 |
| MC58 | 65536 | 32768 | 65536 | 65536 | 65536 | 8192 | 65536 | 32768 | 32768 | 65536 |
| 394/98 | 65536 | 4096 | 16384 | 4096 | 8192 | 4096 | 32768 | 16384 | 8192 | 16384 |

Combination and Comparison with OMVs

In further experiments, the antigens (20 μg of each antigen per dose) were administered in combination with 10 μg OMVs prepared either from strain H44/76 (Norway) or strain 394/98 (New Zealand). Positive controls were the anti-capsular SEAM-3 mAb for serogroup B or CRM197-conjugated capsular saccharides for other strains. The mixture almost always gave better titres than simple OMVs, and addition of the mixture to OMVs almost always significantly enhanced the efficacy of the OMVs. In many cases the antigen mixture matched or exceeded the response seen with the positive control.

Hypervirulent Lineage Tests

The following antigens were tested against a variety of serogroup B strains from a variety of hypervirulent lineages:

(a) NadA(NL)(C)
(b) ΔG287-953
(c) 936-ΔG741
(d) a mixture of (a), (b) and (c)
(e) OMVs prepared from strain H44/76 (Norway)
(f) OMVs prepared from strain 394/98 (New Zealand)
(g) A mixture of ΔG287 and (e)
(h) A mixture of (d) and (e)
(i) A mixture of (d) and (f)
SEAM-3 was used as a positive control.

Results were as follows, expressed as the percentage of strains in the indicated hypervirulent lineage where the serum bactericidal titre exceeded 1024:

| | # strains | (a) | (b) | (c) | (d) | (e) | (f) | (g) | (h) | (i) | S-3 |
|---|---|---|---|---|---|---|---|---|---|---|---|
| A4 | 4 | 50 | 50 | 0 | 100 | 25 | 25 | 25 | 100 | 100 | + |
| ET-5 | 8 | 25 | 75 | 88 | 100 | 71 | 14 | 71 | 100 | 100 | + |
| Lineage 3 | 13 | 0 | 75 | 15 | 93 | 8 | 85 | 8 | 92 | 93 | + |
| ET-37 | 4 | 11 | 22 | 0 | 33 | 0 | 0 | 0 | 22 | 25 | + |

Against particular reference strains, bactericidal titres were as follows:

| | Strain | (a) | (b) | (c) | (d) | (e) | (f) | (g) | (h) | (i) | S-3 |
|---|---|---|---|---|---|---|---|---|---|---|---|
| A4 | 961-5945 | 128 | 2048 | <8 | 2048 | 262144 | 8192 | 262144 | 262144 | 4096 | 8192 |
| ET-5 | 44/76 | <4 | 2048 | 32768 | 131072 | 524288 | 8192 | 524288 | 524288 | 524288 | 16384 |
| Lineage 3 | 394/98 | <4 | 1024 | 32 | 4096 | <4 | 16384 | 256 | 16384 | 16384 | 16384 |
| ET-37 | LPN17592 | 2048 | 1024 | 256 | 4096 | <8 | <8 | 512 | 16384 | 65536 | 1024 |

Compositions (d), (h) and (i) therefore induce bactericidal antibody responses against a wide variety of strains of serogroup B meningococcus from within hypervirulent lineages A4, ET-5 and lineage 3. Titres using compositions (h) and (i) were generally higher than with (d), but the coverage of strains within hypervirulent lineages A4, ET-5 and lineage 3 were no better.

Coverage of untyped strains was also high with compositions (d), (h) and (i).

Combination with Meningococcal and/or Hib Conjugates

The triple MenB composition is combined with a mixture of oligosaccharide conjugates for serogroups C, W135 and Y, to give a vaccine containing the following antigens:

| Component | Quantity per 0.5 ml dose |
| --- | --- |
| Serogroup C conjugate | 10 μg saccharide + 12.5-25 μg $CRM_{197}$ |
| Serogroup W135 conjugate | 10 μg saccharide + 6.6-20 μg $CRM_{197}$ |
| Serogroup Y conjugate | 10 μg saccharide + 6.6-20 μg $CRM_{197}$ |
| ΔG287-953 | 20 μg polypeptide |
| 936-ΔG741 | 20 μg polypeptide |
| NadA | 20 μg polypeptide |

A similar vaccine is prepared, including MenA conjugate (10 μg saccharide+12.5-33 μg $CRM_{197}$) and/or a HbOC Hib conjugate (10 μg saccharide+2-5 μg $CRM_{197}$).

In one series of tests, conjugates of serogroups C, W135 and Y were combined, with each conjugate present at 40 μg/ml (measured as saccharide). For storage prior to use with MenB antigens the combined conjugates were lyophilised [−45° C. for 3 hours, −35° C. for 20 hours at 50 mTorr vacuum, 30° C. for 10 hours at 50 mTorr, 30° C. for 9 hours at 125 mTorr] in the presence of 15 mg sucrose, 10 mM phosphate buffer (pH 7.2). The final volume before lyophilisation was 0.3 ml. After resuspension in 0.6 ml aqueous solution, therefore, the saccharides are present at 12 μg per serogroup. Lyophilisation was used for convenience only, and neither efficacy nor stability during normal storage of the final product requires lyophilisation.

A second batch of material was prepared in the same way, but including also the serogroup A conjugate at the same saccharide dosage as for serogroups C, W135 and Y.

A third batch of material was prepared in the same way (serogroups A, C, W135 and Y), but including also a Hib-$CRM_{197}$ conjugate at the same saccharide dosage as for the meningococci.

For comparison, lyophilised preparations of the serogroup A and C conjugates were prepared. The MenA material was lyophilised with 15 mg sucrose to give a 12 μg dose of saccharide after reconstitution, as described above. The MenC material was lyophilised with 9 mg mannitol to give a 12 μg dose of saccharide after reconstitution.

These materials were combined with 600 μl of the serogroup mixture (d) (or, as a control, i.e. groups 2 & 3, in an identical composition but lacking the antigens), to give eight compositions:

| Components | 1 | 2 | 3 | 4 | 5 | 6 | 7 | 8 |
| --- | --- | --- | --- | --- | --- | --- | --- | --- |
| $NadA^{(NL)(C)}$ μg/dose | 20 | | | 20 | 20 | 20 | 20 | 20 |
| 936-741 μg/dose | 20 | | | 20 | 20 | 20 | 20 | 20 |
| 287-953 μg/dose | 20 | | | 20 | 20 | 20 | 20 | 20 |
| MenA-CRM μg/dose* | | 2.4 | 2.4 | 2.4 | | | 2.4 | 2.4 |
| MenC-CRM μg/dose* | | 2.4 | 2.4 | | 2.4 | 2.4 | 2.4 | 2.4 |
| MenW-CRM μg/dose* | | 2.4 | 2.4 | | | 2.4 | 2.4 | 2.4 |
| MenY-CRM μg/dose* | | 2.4 | 2.4 | | | 2.4 | 2.4 | 2.4 |
| Hib-CRM μg/dose* | | | 2.4 | | | | | 2.4 |
| Aluminium hydroxide mg/dose | 0.15 | 0.15 | 0.15 | 0.15 | 0.15 | 0.15 | 0.15 | 0.15 |
| Histidine mM | 10 | 10 | 10 | 10 | 10 | 10 | 10 | 10 |
| Sucrose mg/dose | | 3 | 3 | 3 | | 3 | 3 | 3 |
| Mannitol mg/dose | | | | | 1.8 | | | |
| Potassium phosphate pH 7.2 mM | | 3 | 3 | 3 | | 3 | 3 | 3 |
| Sodium Phosphate pH 7.2 mM | | | | | 3 | | | |
| Sodium chloride mg/dose | 1.8 | 1.8 | 1.8 | 1.8 | 1.8 | 1.8 | 1.8 | 1.8 |

*Quantity shown is saccharide

These compositions were administered intraperitoneally in a volume of 200 μl to CD/1 mice (8 per group) on days 0, 21 and 35, with a final bleed at day 49. The day 49 sera were tested in SBA assays against a variety of meningococcal strains in serogroups A, B, C, W135 and Y. Results were:

| | Group | | | | | | | | | |
| --- | --- | --- | --- | --- | --- | --- | --- | --- | --- | --- |
| | B | | | | A | C | | | W135 | Y |
| | 2996 | MC5B | 394/98 | 44/76 | F6124 | C11 | 312294 | C4678 | M1569 | LPN17592 | 860800 |
| 1 | 1024 | 4096 | 1024 | 8192 | 2048 | 2048 | <16* | 64* | 128* | 512 | 65536 |
| 2 | <4 | <4 | 128 | <16 | 4096 | 8192 | — | — | — | 32 | 32768 |
| 3 | <4 | <4 | <4 | <16 | 4096 | 16384 | — | — | — | 512 | 32768 |
| 4 | 64 | 4096 | 512 | 8192 | 8192 | 128 | — | — | — | 256 | 32768 |
| 5 | 256 | 4096 | 1024 | 8192 | 256 | 8192 | >8192 | >8192 | >8192 | 512 | 32768 |
| 6 | 128 | 1024 | 256 | 8192 | 128 | 8192 | 8192 | >8192 | >8192 | 512 | 16384 |
| 7 | 256 | 512 | 512 | 16384 | 1024 | 8192 | 4096 | >8192 | >8192 | 1024 | 16384 |
| 8 | 256 | 2048 | 512 | 8192 | 1024 | 8192 | 2048 | >8192 | >8192 | 512 | 32768 |

Thus the meningococcal protein antigens remain effective even after addition of the conjugated meningococcal and Hib saccharide antigens. Similarly, the meningococcal conjugates retain efficacy even after addition of the protein antigens. Indeed, the data suggest that the addition of the protein antigens to the conjugates enhances the anti-MenW135 efficacy (compare groups 2 and 7). Moreover, there is a level of cross-reactivity, in particular for serogroup Y, as the protein antigens alone give a good anti-MenY titre [cf. reference 220], as do groups 4 and 5.

The data also indicate that addition of a Hib conjugate to meningococcal conjugates (compare groups 2 and 3) enhances the anti-W135 activity.

Use of Modified MenA Saccharide

Capsular polysaccharide was purified from MenA and was hydrolysed to give MenA oligosaccharide. The polysaccharide (2 g) was hydrolyzed at 50° C. in 50 mM sodium acetate buffer, pH 4.75, at a polysaccharide concentration of 10 mg/mL for about 4 hours [73]. After hydrolysis, the solution was dried by rotary evaporation.

The oligosaccharide was activated using the following reaction scheme:

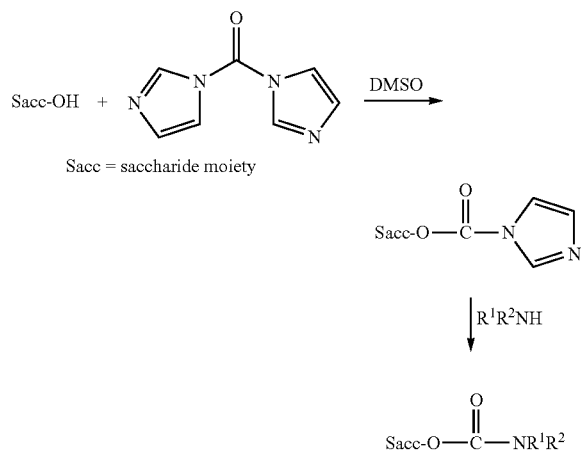

The oligosaccharide was dissolved in DMSO to give a saccharide concentration of 10 mg/mL. According to a molar ratio of oligosaccharide:CDI being 1:20, 21.262 g of CDI was then added and the reaction mixture stirred for 16 hours at room temperature. The resulting MenA-CDI compound was purified by selective precipitation in a 80:20 (v/v) acetone:DMSO mixture followed by centrifugation. The efficiency of the activation reaction was calculated to be about 67.9% by determining the ratio of free imidazole to bonded imidazole.

In the second reaction step, the MenA-CDI oligosaccharide was solubilised in DMSO at a saccharide concentration of about 10 mg/mL. According to a molar ratio of MenA-CDI unit:DMA being 1:100, 36.288 g of 99% dimethylamine hydrochloride (i.e. $R^1$ & $R^2$=Me) was added and the reaction mixture stirred for 16 hours at room temperature. The reaction product was freeze-dried and re-solubilised in 10 mg/mL water solution.

To remove the low molecular weight reaction reagent (in particular the dimethylamine (DMA)) from the oligosaccharide preparation, a dialysis step was performed through a 3.5 kDa MWCO membrane (Spectra/Por™). Four dialysis steps were carried out: (i) 16 hours against 2 L of 1 M sodium chloride (dialysis factor 1:20), (ii) 16 hours against 2 L of 0.5 M sodium chloride (dialysis factor 1:20), (iii) and (iv) 16 hours against 2 L of WFI (dialysis factor 1:20). To improve the purification a diafiltration step was also performed through a 1 kDa MWCO membrane (Centricon™).

The purified MenA-CDI-DMA product was buffered at pH 6.5 in 25 mM L-histidine (Fluka™).

For preparing conjugates of the modified MenA saccharide (MenA-CDI-DMA), the overall process was as follows:
- hydrolysis of the polysaccharide to give oligosaccharide fragments
- sizing of the oligosaccharide fragments
- reductive amination of terminal aldehyde groups on the sized oligosaccharides
- protection of terminal —$NH_2$ groups by Fmoc group before the CDI reaction
- intrinsic de-protection of —$NH_2$ groups during the DMA reaction
- activation of terminal —$NH_2$ groups by SIDEA (N-hydroxysuccinimide adipic acid)
- covalent attachment to $CRM_{197}$ protein The modified MenA oligosaccharide conjugate was much more resistant to hydrolysis than its natural counterpart at elevated temperatures. After 28 days at 37° C., for instance, the percentage of released saccharide is 6.4% for the modified oligosaccharide vs. 23.5% for the natural antigen. Moreover, the titres induced by the modified oligosaccharides are not significantly lower than those obtained using the native sugar structures.

The modified MenA conjugate is combined with MenC, MenW135 and MenY conjugates as a substitute for the conjugate of unmodified oligosaccharide. This tetravalent mixture is mixed with the three MenB polypeptides to give a vaccine effective against serogroups A, B, C, W135 and Y of *N. meningitidis* in a single dose.

Pneumococcal Combinations

The three combined MenB proteins are mixed with pneumococcal saccharide conjugates to give a final concentration of 2 μg/dose of each of the pneumococcal serotypes (double for serotype 6B). The reconstituted vaccine thus contains the following antigens:

| Component | Quantity per 0.5 ml dose |
|---|---|
| Serogroup A conjugate | 5 μg saccharide + 6.25-16.5 μg $CRM_{197}$ |
| Serogroup C conjugate | 5 μg saccharide + 6.25-12.5 μg $CRM_{197}$ |
| Serogroup W135 conjugate | 5 μg saccharide + 3.3-10 μg $CRM_{197}$ |
| Serogroup Y conjugate | 5 μg saccharide + 3.3-10 μg $CRM_{197}$ |
| *Pneumococcus* serotype 4 conjugate | 2 μg saccharide + 2.5 μg $CRM_{197}$ |
| *Pneumococcus* serotype 9V conjugate | 2 μg saccharide + 2.5 μg $CRM_{197}$ |
| *Pneumococcus* serotype 14 conjugate | 2 μg saccharide + 2.5 μg $CRM_{197}$ |
| *Pneumococcus* serotype 18C conjugate | 2 μg saccharide + 2.5 μg $CRM_{197}$ |
| *Pneumococcus* serotype 19F conjugate | 2 μg saccharide + 2.5 μg $CRM_{197}$ |
| *Pneumococcus* serotype 23F conjugate | 2 μg saccharide + 2.5 μg $CRM_{197}$ |
| *Pneumococcus* serotype 6B conjugate | 4 μg saccharide + 5 μg $CRM_{197}$ |

It will be understood that the invention has been described by way of example only and modifications may be made whilst remaining within the scope and spirit of the invention.

REFERENCES

The Contents of which are Hereby Incorporated by Reference

[1] Darkes & Plosker (2002) *Paediatr Drugs* 4:609-630.
[2] Jones (2001) *Curr Opin Investig Drugs* 2:47-49.
[3] Armand et al. (1982) *J. Biol. Stand.* 10:335-339.
[4] Cadoz et al. (1985) *Vaccine* 3:340-342.
[5] Baklaic et al. (1983) *Infect. Immun.* 42:599-604.

[6] MMWR (1997) 46(RR-5) 1-10.
[7] Bjune et al. (1991) *Lancet* 338(8775):1093-96
[8] Frash (1990) p. 123-145 of *Advances in Biotechnological Processes* vol. 13 (eds. Mizrahi & Van Wezel)
[9] WO03/007985.
[10] Inzana (1987) *Infect. Immun.* 55:1573-1579.
[11] WO02/058737.
[12] UK patent application GB-0408978.5. [attorney ref: P037501GB].
[13] Kandil et al. (1997) *Glycoconj J* 14:13-17.
[14] Berkin et al. (2002) *Chemistry* 8:4424-4433.
[15] Glode et al. (1979) *J Infect Dis* 139:52-56
[16] WO94/05325; U.S. Pat. No. 5,425,946.
[17] PCT/IB2004/003366, filed 4 Oct. 2004 claiming priority from UK patent application GB-0323103.2.
[18] WO03/080678.
[19] Nilsson & Svensson (1979) *Carbohydrate Research* 69: 292-296)
[20] Ramsay et al. (2001) *Lancet* 357(9251):195-196.
[21] Lindberg (1999) *Vaccine* 17 Suppl 2:S28-36.
[22] Buttery & Moxon (2000) *J R Coll Physicians Lond* 34:163-168.
[23] Ahmad & Chapnick (1999) *Infect Dis Clin North Am* 13:113-133, vii.
[24] Goldblatt (1998) *J. Med. Microbiol.* 47:563-567.
[25] European patent 0477508.
[26] U.S. Pat. No. 5,306,492.
[27] WO98/42721.
[28] *Conjugate Vaccines* (eds. Cruse et al.) ISBN 3805549326, particularly vol. 10:48-114.
[29] Hermanson (1996) *Bioconjugate Techniques* ISBN: 0123423368 or 012342335X.
[30] Anonymous (January 2002) *Research Disclosure*, 453077.
[31] Anderson (1983) *Infect Immun* 39(1):233-238.
[32] Anderson et al. (1985) *J Clin Invest* 76(1):52-59.
[33] EP-A-0372501.
[34] EP-A-0378881.
[35] EP-A-0427347.
[36] WO93/17712
[37] WO94/03208.
[38] WO98/58668.
[39] EP-A-0471177.
[40] WO91/01146
[41] Falugi et al. (2001) *Eur J Immunol* 31:3816-3824.
[42] Baraldo et al, (2004) *Infect Immun.* 72:4884-7
[43] EP-A-0594610.
[44] WO00/56360.
[45] Kuo et al. (1995) *Infect Immun* 63:2706-13.
[46] WO02/091998.
[47] WO01/72337.
[48] WO00/61761.
[49] WO2004/083251.
[50] WO99/42130
[51] WO96/40242
[52] Lees et al. (1996) *Vaccine* 14:190-198.
[53] WO95/08348.
[54] U.S. Pat. No. 4,882,317
[55] U.S. Pat. No. 4,695,624
[56] Porro et al. (1985) *Mol Immunol* 22:907-919.
[57] EP-A-0208375
[58] WO00/10599
[59] Gever et al. Med. Microbiol. Immunol, 165: 171-288 (1979).
[60] U.S. Pat. No. 4,057,685.
[61] U.S. Pat. Nos. 4,673,574; 4,761,283; 4,808,700.
[62] U.S. Pat. No. 4,459,286.
[63] U.S. Pat. No. 4,965,338
[64] U.S. Pat. No. 4,663,160.
[65] U.S. Pat. No. 4,761,283
[66] U.S. Pat. No. 4,356,170
[67] Lei et al. (2000) *Dev Biol (Basel)* 103:259-264.
[68] WO00/38711; U.S. Pat. No. 6,146,902.
[69] Lamb et al. (2000) *Dev Biol (Basel)* 103:251-258.
[70] Lamb et al. (2000) *Journal of Chromatography A* 894:311-318.
[71] D'Ambra et al. (2000) *Dev Biol (Basel)* 103:241-242.
[72] Ravenscroft et al. (1999) *Vaccine* 17:2802-2816.
[73] Costantino et al. (1999) *Vaccine* 17:1251-1263.
[74] Parkhill et al. (2000) *Nature* 404:502-506.
[75] Tettelin et al. (2000) *Science* 287:1809-1815.
[76] WO00/66791.
[77] Pizza et al. (2000) *Science* 287:1816-1820.
[78] WO99/24578.
[79] WO99/36544.
[80] WO99/57280.
[81] WO00/22430.
[82] WO00/66741.
[83] WO01/64920.
[84] WO01/64922.
[85] WO03/020756.
[86] WO2004/014419.
[87] WO99/31132; U.S. Pat. No. 6,495,345.
[88] WO99/58683.
[89] Peak et al. (2000) *FEMS Immunol Med Microbiol* 28:329-334.
[90] WO93/06861.
[91] EP-A-0586266.
[92] WO92/03467.
[93] U.S. Pat. No. 5,912,336.
[94] WO2004/015099.
[95] WO2004/014418.
[96] UK patent applications 0223741.0, 0305831.0 & 0309115.4; and WO2004/032958.
[97] Comanducci et al. (2002) *J. Exp. Med* 195:1445-1454.
[98] WO03/010194.
[99] WO2004/048404
[100] WO03/063766.
[101] Masignani et al. (2003) *J Exp Med* 197:789-799.
[102] http://*neisseria*.org/nm/typing/mlst/
[103] Pettersson et al. (1994) *Microb Pathog* 17(6):395-408.
[104] Maiden et al. (1998) *PNAS USA* 95:3140-3145.
[105] Welsch et al. (2002) Thirteenth International Pathogenic *Neisseria* Conference, Norwegian Institute of Public Health, Oslo, Norway; Sep. 1-6, 2002. *Genome-derived antigen (GNA) 2132 elicits protective serum antibodies to groups B and C Neisseria meningitidis strains.*
[106] Santos et al. (2002) Thirteenth International Pathogenic *Neisseria* Conference, Norwegian Institute of Public Health, Oslo, Norway; Sep. 1-6, 2002. *Serum bactericidal responses in rhesus macaques immunized with novel vaccines containing recombinant proteins derived from the genome of N. meningitidis.*
[107] WO96/14086.
[108] *Vaccines* (eds. Plotkin & Mortimer), 1988. ISBN: 0-7216-1946-0
[109] Gustafsson et al. (1996) *N. Engl. J. Med.* 334:349-355.
[110] Rappuoli et al. (1991) *TIBTECH* 9:232-238.
[111] Bell (2000) *Pediatr Infect Dis J* 19:1187-1188.
[112] Iwarson (1995) *APMIS* 103:321-326.
[113] Gerlich et al. (1990) *Vaccine* 8 Suppl:S63-68 & 79-80.

[114] WO93/24148.
[115] Sutter et al. (2000) *Pediatr Clin North Am* 47:287-308.
[116] Zimmerman & Spann (1999) *Am Fam Physician* 59:113-118, 125-126.
[117] Charalambous & Feavers (2001) *J Med Microbiol* 50:937-939.
[118] Westerink (2001) *Int Rev Immunol* 20:251-261.
[119] Grothaus et al. (2000) *Vaccine* 18:1253-1263.
[120] Kanra et al. (1999) *The Turkish Journal of Paediatrics* 42:421-427.
[121] Ravenscroft et al. (2000) *Dev Biol (Basel)* 103:35-47.
[122] WO97/00697.
[123] WO02/00249.
[124] WO96/37222; U.S. Pat. No. 6,333,036.
[125] Watson (2000) *Pediatr Infect Dis J* 19:331-332.
[126] Rubin (2000) *Pediatr Clin North Am* 47:269-285, v.
[127] Jedrzejas (2001) *Microbiol Mol Biol Rev* 65:187-207.
[128] Zielen et al. (2000) *Infect. Immun.* 68:1435-1440.
[129] Tettelin et al. (2001) *Science* 293:498-506.
[130] Hoskins et al (2001) *J Bacteriol* 183:5709-5717.
[131] Rappuoli (2000) *Curr Opin Microbiol* 3:445-450
[132] Rappuoli (2001) *Vaccine* 19:2688-2691.
[133] Masignani et al. (2002) *Expert Opin Biol Ther* 2:895-905.
[134] Mora et al. (2003) *Drug Discov Today* 8:459-464.
[135] Wizemann et al. (2001) *Infect Immun* 69:1593-1598.
[136] Rigden et al. (2003) *Crit Rev Biochem Mol Biol* 38:143-168.
[137] WO02/22167.
[138] Paoleti et al. (2001) *Vaccine* 19:2118-2126.
[139] WO00/56365.
[140] Gennaro (2000) *Remington: The Science and Practice of Pharmacy.* 20th edition, ISBN: 0683306472.
[141] WO03/009869.
[142] *Vaccine Design* . . . (1995) eds. Powell & Newman. ISBN: 030644867X. Plenum.
[143] WO00/23105.
[144] WO90/14837.
[145] U.S. Pat. No. 5,057,540.
[146] WO96/33739.
[147] EP-A-0109942.
[148] WO96/11711.
[149] WO00/07621.
[150] Barr et al. (1998) *Advanced Drug Delivery Reviews* 32:247-271.
[151] Sjolanderet et al. (1998) *Advanced Drug Delivery Reviews* 32:321-338.
[152] Niikura et al. (2002) *Virology* 293:273-280.
[153] Lenz et al. (2001) *J Immunol* 166:5346-5355.
[154] Pinto et al. (2003) *J Infect Dis* 188:327-338.
[155] Gerber et al. (2001) *Virol* 75:4752-4760.
[156] WO03/024480
[157] WO03/024481
[158] Gluck et al. (2002) *Vaccine* 20:B10-B16.
[159] EP-A-0689454.
[160] Johnson et al. (1999) *Bioorg Med Chem Lett* 9:2273-2278.
[161] Evans et al. (2003) *Expert Rev Vaccines* 2:219-229.
[162] Meraldi et al. (2003) *Vaccine* 21:2485-2491.
[163] Pajak et al. (2003) *Vaccine* 21:836-842.
[164] Kandimalla et al. (2003) *Nucleic Acids Research* 31:2393-2400.
[165] WO02/26757.
[166] WO99/62923.
[167] Krieg (2003) *Nature Medicine* 9:831-835.
[168] McCluskie et al. (2002) *FEMS Immunology and Medical Microbiology* 32:179-185.
[169] WO98/40100.
[170] U.S. Pat. No. 6,207,646.
[171] U.S. Pat. No. 6,239,116.
[172] U.S. Pat. No. 6,429,199.
[173] Kandimalla et al. (2003) *Biochemical Society Transactions* 31 (part 3):654-658.
[174] Blackwell et al. (2003) *J Immunol* 170:4061-4068.
[175] Krieg (2002) *Trends Immunol* 23:64-65.
[176] WO01/95935.
[177] Kandimalla et al. (2003) *BBRC* 306:948-953.
[178] Bhagat et al. (2003) *BBRC* 300:853-861.
[179] WO03/035836.
[180] WO95/17211.
[181] WO98/42375.
[182] Beignon et al. (2002) *Infect Immun* 70:3012-3019.
[183] Pizza et al. (2001) *Vaccine* 19:2534-2541.
[184] Pizza et al. (2000) *Int J Med Microbiol* 290:455-461.
[185] Scharton-Kersten et al. (2000) *Infect Immun* 68:5306-5313.
[186] Ryan et al. (1999) *Infect Immun* 67:6270-6280.
[187] Partidos et al. (1999) *Immunol Lett* 67:209-216.
[188] Peppoloni et al. (2003) *Expert Rev Vaccines* 2:285-293.
[189] Pine et al. (2002) *J Control Release* 85:263-270.
[190] Domenighini et al. (1995) *Mol Microbiol* 15:1165-1167.
[191] WO99/40936.
[192] WO99/44636.
[193] Singh et al] (2001) *J Cont Release* 70:267-276.
[194] WO99/27960.
[195] U.S. Pat. No. 6,090,406
[196] U.S. Pat. No. 5,916,588
[197] EP-A-0626169.
[198] WO99/52549.
[199] WO01/21207.
[200] WO01/21152.
[201] Andrianov et al. (1998) *Biomaterials* 19:109-115.
[202] Payne et al. (1998) *Adv Drug Delivery Review* 31:185-196.
[203] Stanley (2002) *Clin Exp Dermatol* 27:571-577.
[204] Jones (2003) *Curr Opin Investig Drugs* 4:214-218.
[205] WO99/11241.
[206] WO94/00153.
[207] WO98/57659.
[208] European patent applications 0835318, 0735898 and 0761231.
[209] WO01/30390.
[210] Almeida & Alpar (1996) *J. Drug Targeting* 3:455-467.
[211] Agarwal & Mishra (1999) *Indian J Exp Biol* 37:6-16.
[212] WO00/53221.
[213] Jakobsen et al. (2002) *Infect Immun* 70:1443-1452.
[214] Wu et al. (1997) *J Infect Dis* 175:839-846.
[215] Bergquist et al. (1998) *APMIS* 106:800-806.
[216] Baudner et al. (2002) *Infect Immun* 70:4785-4790.
[217] Ugozzoli et al. (2002) *J Infect Dis* 186:1358-1361.
[218] *Current Protocols in Molecular Biology* (F. M. Ausubel et al., eds., 1987) Supplement 30.
[219] Smith & Waterman (1981) *Adv. Appl. Math.* 2: 482-489.
[220] UK patent application 0408977.7. [attorney ref: P037500GB].

The invention claimed is:

1. An aqueous immunogenic composition which, after administration to a subject, is able to induce an immune response that is bactericidal against serogroups B, C, W135 and Y of *N. meningitidis*, wherein the composition comprises: (i) a conjugated serogroup C capsular saccharide antigen; (ii) a conjugated serogroup W135 capsular saccharide antigen; (iii) a conjugated serogroup Y capsular saccharide antigen; and (iv) a 'NadA' protein in oligomeric form, a '741' protein, a '936' protein, a '953' protein and a '287'' protein, wherein:
the NadA has an amino acid sequence which has 80% or more identity to SEQ ID NO:2;
the 741 has an amino acid sequence which has 80% or more identity to SEQ ID NO:3;
the 936 has an amino acid sequence which has 80% or more identity to SEQ ID NO:4; and
(a) the 953 has an amino acid sequence which has 80% or more identity to SEQ ID NO:5; and
the 287 has an amino acid sequence which has 80% or more identity to SEQ ID NO:6; or (b) the 953 and the 287 form a contiguous polypeptide having an amino acid sequence which has 80% or more identity to SEQ ID NO: 7.

2. The composition of claim 1, further comprising: (v) a conjugated serogroup A capsular saccharide antigen.

3. The composition of claim 2, wherein the serogroup A capsular saccharide is modified such that at least 20% of its monosaccharide units do not have —OH at either of the 3 and 4 positions.

4. The composition of claim 1, wherein the conjugated saccharides are oligosaccharides.

5. The composition of claim 1, wherein the saccharides are conjugated to a carrier protein selected from: diphtheria toxoid, tetanus toxoid, *H. influenzae* protein D, and $CRM_{197}$.

6. The composition of claim 1, comprising: a first polypeptide comprising amino acid sequence SEQ ID NO:2; a second polypeptide comprising amino acid sequence SEQ ID NO:7; and a third polypeptide comprising amino acid sequence SEQ ID NO:8.

7. The composition of claim 1, further comprising a saccharide antigen that protects against *H. influenzae* type B (Hib).

8. The composition of claim 1, further comprising an antigen that protects against *Streptococcus pneumoniae*.

9. The composition of claim 1 comprising an aluminium phosphate adjuvant.

10. The composition of claim 1, packaged in a hermetically-sealed container.

11. The composition of claim 10, wherein the container is a vial or a syringe.

12. A method for raising an antibody response in a mammal, comprising administering a composition of claim 1 to the mammal.

13. The composition of claim 1, wherein:
the NadA has an amino acid sequence which has 90% or more identity to SEQ ID NO:2;
the 741 has an amino acid sequence which has 90% or more identity to SEQ ID NO:3;
the 936 has an amino acid sequence which has 90% or more identity to SEQ ID NO:4;
the 953 has an amino acid sequence which has 90% or more identity to SEQ ID NO:5; and
the 287 has an amino acid sequence which has 90% or more identity to SEQ ID NO:6.

14. The composition of claim 1, wherein:
the NadA has an amino acid sequence which has 95% or more identity to SEQ ID NO:2;
the 741 has an amino acid sequence which has 95% or more identity to SEQ ID NO:3;
the 936 has an amino acid sequence which has 95% or more identity to SEQ ID NO:4;
the 953 and the 287 form a contiguous polypeptide having an amino acid sequence which has 95% or more identity to SEQ ID NO: 7.

15. An aqueous immunogenic composition which comprises: (i) a conjugated serogroup C capsular saccharide antigen; (ii) a conjugated serogroup W135 capsular saccharide antigen; (iii) a conjugated serogroup Y capsular saccharide antigen; and (iv) a 'NadA' protein in oligomeric form, a '741' protein, a '936' protein, a '953' protein and a '287'' protein, wherein:
the NadA has an amino acid sequence which has 80% or more identity to SEQ ID NO:2;
the 741 has an amino acid sequence which has 80% or more identity to SEQ ID NO:3;
the 936 has an amino acid sequence which has 80% or more identity to SEQ ID NO:4;
the 953 has an amino acid sequence which has 80% or more identity to SEQ ID NO:5; and
the 287 has an amino acid sequence which has 80% or more identity to SEQ ID NO:6.

* * * * *

SEQUENCE LISTING

<160> NUMBER OF SEQ ID NOS: 12

<210> SEQ ID NO 1
<211> LENGTH: 350
<212> TYPE: PRT
<213> ORGANISM: N. meningitidis

<400> SEQUENCE: 1

Met Lys His Phe Pro Ser Lys Val Leu Thr Thr Ala Ile Leu Ala Thr
1               5                   10                  15

Phe Cys Ser Gly Ala Leu Ala Ala Thr Asn Asp Asp Val Lys Lys
            20                  25                  30

Ala Ala Thr Val Ala Ile Ala Ala Tyr Asn Asn Gly Gln Glu Ile
            35                  40                  45

Asn Gly Phe Lys Ala Gly Glu Thr Ile Tyr Asp Ile Asp Glu Asp Gly
    50                  55                  60

Thr Ile Thr Lys Lys Asp Ala Thr Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
            115                 120                 125

Leu Ala Asp Thr Asp Ala Ala Leu Asp Ala Thr Thr Asn Ala Leu Asn
130                 135                 140

Lys Leu Gly Glu Asn Ile Thr Thr Phe Ala Glu Thr Lys Thr Asn
145                 150                 155                 160

Ile Val Lys Ile Asp Glu Lys Leu Glu Ala Val Ala Asp Thr Val Asp
                165                 170                 175

Lys His Ala Glu Ala Phe Asn Asp Ile Ala Asp Ser Leu Asp Glu Thr
            180                 185                 190

Asn Thr Lys Ala Asp Glu Ala Val Lys Thr Ala Asn Glu Ala Lys Gln
            195                 200                 205

Thr Ala Glu Glu Thr Lys Gln Asn Val Asp Ala Lys Val Lys Ala Ala
210                 215                 220

Glu Thr Ala Ala Gly Lys Ala Glu Ala Ala Gly Thr Ala Asn Thr
225                 230                 235                 240

Ala Ala Asp Lys Ala Glu Ala Val Ala Ala Lys Val Thr Asp Ile Lys
                245                 250                 255

Ala Asp Ile Ala Thr Asn Lys Asp Asn Ile Ala Lys Lys Ala Asn Ser
            260                 265                 270

Ala Asp Val Tyr Thr Arg Glu Glu Ser Asp Ser Lys Phe Val Arg Ile
            275                 280                 285

Asp Gly Leu Asn Ala Thr Thr Glu Lys Leu Asp Thr Arg Leu Ala Ser
        290                 295                 300

Ala Glu Lys Ser Ile Ala Asp His Asp Thr Arg Leu Asn Gly Leu Asp
305                 310                 315                 320

Lys Thr Val Ser Asp Leu Arg Lys Glu Thr Arg Gln Gly Leu Ala Glu
                325                 330                 335

Gln Ala Ala Leu Ser Gly Leu Phe Gln Pro Tyr Asn Val Gly
            340                 345                 350

```
<210> SEQ ID NO 2
<211> LENGTH: 327
<212> TYPE: PRT
<213> ORGANISM: N. meningitidis

<400> SEQUENCE: 2

Ala Thr Asn Asp Asp Val Lys Lys Ala Thr Val Ala Ile Ala
1               5                   10                  15

Ala Ala Tyr Asn Asn Gly Gln Glu Ile Asn Gly Phe Lys Ala Gly Glu
            20                  25                  30

Thr Ile Tyr Asp Ile Asp Glu Asp Gly Thr Ile Thr Lys Lys Asp Ala
                35                  40                  45

Thr Ala Ala Asp Val Glu Ala Asp Phe Lys Gly Leu Gly Leu Lys
    50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
            115                 120                 125

Thr Phe Ala Glu Glu Thr Lys Thr Asn Ile Val Lys Ile Asp Glu Lys
    130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
            195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
            275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325

<210> SEQ ID NO 3
<211> LENGTH: 248
<212> TYPE: PRT
<213> ORGANISM: N. meningitidis
```

```
<400> SEQUENCE: 3

Val Ala Ala Asp Ile Gly Ala Gly Leu Ala Asp Ala Leu Thr Ala Pro
1               5                   10                  15

Leu Asp His Lys Asp Lys Gly Leu Gln Ser Leu Thr Leu Asp Gln Ser
            20                  25                  30

Val Arg Lys Asn Glu Lys Leu Lys Leu Ala Ala Gln Gly Ala Glu Lys
        35                  40                  45

Thr Tyr Gly Asn Gly Asp Ser Leu Asn Thr Gly Lys Leu Lys Asn Asp
    50                  55                  60

Lys Val Ser Arg Phe Asp Phe Ile Arg Gln Ile Glu Val Asp Gly Gln
65                  70                  75                  80

Leu Ile Thr Leu Glu Ser Gly Glu Phe Gln Val Tyr Lys Gln Ser His
                85                  90                  95

Ser Ala Leu Thr Ala Phe Gln Thr Glu Gln Ile Gln Asp Ser Glu His
            100                 105                 110

Ser Gly Lys Met Val Ala Lys Arg Gln Phe Arg Ile Gly Asp Ile Ala
        115                 120                 125

Gly Glu His Thr Ser Phe Asp Lys Leu Pro Glu Gly Gly Arg Ala Thr
    130                 135                 140

Tyr Arg Gly Thr Ala Phe Gly Ser Asp Asp Ala Gly Gly Lys Leu Thr
145                 150                 155                 160

Tyr Thr Ile Asp Phe Ala Ala Lys Gln Gly Asn Gly Lys Ile Glu His
                165                 170                 175

Leu Lys Ser Pro Glu Leu Asn Val Asp Leu Ala Ala Ala Asp Ile Lys
            180                 185                 190

Pro Asp Gly Lys Arg His Ala Val Ile Ser Gly Ser Val Leu Tyr Asn
        195                 200                 205

Gln Ala Glu Lys Gly Ser Tyr Ser Leu Gly Ile Phe Gly Gly Lys Ala
    210                 215                 220

Gln Glu Val Ala Gly Ser Ala Glu Val Lys Thr Val Asn Gly Ile Arg
225                 230                 235                 240

His Ile Gly Leu Ala Ala Lys Gln
                245

<210> SEQ ID NO 4
<211> LENGTH: 179
<212> TYPE: PRT
<213> ORGANISM: N. meningitidis

<400> SEQUENCE: 4

Val Ser Ala Val Ile Gly Ser Ala Ala Val Gly Ala Lys Ser Ala Val
1               5                   10                  15

Asp Arg Arg Thr Thr Gly Ala Gln Thr Asp Asp Asn Val Met Ala Leu
            20                  25                  30

Arg Ile Glu Thr Thr Ala Arg Ser Tyr Leu Arg Gln Asn Asn Gln Thr
        35                  40                  45

Lys Gly Tyr Thr Pro Gln Ile Ser Val Val Gly Tyr Asn Arg His Leu
    50                  55                  60

Leu Leu Leu Gly Gln Val Ala Thr Glu Gly Lys Gln Phe Val Gly
65                  70                  75                  80

Gln Ile Ala Arg Ser Glu Gln Ala Ala Glu Gly Val Tyr Asn Tyr Ile
                85                  90                  95

Thr Val Ala Ser Leu Pro Arg Thr Ala Gly Asp Ile Ala Gly Asp Thr
            100                 105                 110
```

```
Trp Asn Thr Ser Lys Val Arg Ala Thr Leu Leu Gly Ile Ser Pro Ala
            115                 120                 125

Thr Gln Ala Arg Val Lys Ile Val Thr Tyr Gly Asn Val Thr Tyr Val
    130                 135                 140

Met Gly Ile Leu Thr Pro Glu Glu Gln Ala Gln Ile Thr Gln Lys Val
145                 150                 155                 160

Ser Thr Thr Val Gly Val Gln Lys Val Ile Thr Leu Tyr Gln Asn Tyr
                165                 170                 175

Val Gln Arg

<210> SEQ ID NO 5
<211> LENGTH: 168
<212> TYPE: PRT
<213> ORGANISM: N. meningitidis

<400> SEQUENCE: 5

Ala Thr Tyr Lys Val Asp Glu Tyr His Ala Asn Ala Arg Phe Ala Ile
1               5                   10                  15

Asp His Phe Asn Thr Ser Thr Asn Val Gly Gly Phe Tyr Gly Leu Thr
            20                  25                  30

Gly Ser Val Glu Phe Asp Gln Ala Lys Arg Asp Gly Lys Ile Asp Ile
        35                  40                  45

Thr Ile Pro Ile Ala Asn Leu Gln Ser Gly Ser Gln His Phe Thr Asp
    50                  55                  60

His Leu Lys Ser Ala Asp Ile Phe Asp Ala Ala Gln Tyr Pro Asp Ile
65                  70                  75                  80

Arg Phe Val Ser Thr Lys Phe Asn Phe Asn Gly Lys Lys Leu Val Ser
                85                  90                  95

Val Asp Gly Asn Leu Thr Met His Gly Lys Thr Ala Pro Val Lys Leu
            100                 105                 110

Lys Ala Glu Lys Phe Asn Cys Tyr Gln Ser Pro Met Glu Lys Thr Glu
        115                 120                 125

Val Cys Gly Gly Asp Phe Ser Thr Thr Ile Asp Arg Thr Lys Trp Gly
    130                 135                 140

Met Asp Tyr Leu Val Asn Val Gly Met Thr Lys Ser Val Arg Ile Asp
145                 150                 155                 160

Ile Gln Ile Glu Ala Ala Lys Gln
                165

<210> SEQ ID NO 6
<211> LENGTH: 464
<212> TYPE: PRT
<213> ORGANISM: N. meningitidis

<400> SEQUENCE: 6

Ser Pro Asp Val Lys Ser Ala Asp Thr Leu Ser Lys Pro Ala Ala Pro
1               5                   10                  15

Val Val Ser Glu Lys Glu Thr Glu Ala Lys Glu Asp Ala Pro Gln Ala
            20                  25                  30

Gly Ser Gln Gly Gln Gly Ala Pro Ser Ala Gln Gly Ser Gln Asp Met
        35                  40                  45

Ala Ala Val Ser Glu Glu Asn Thr Gly Asn Gly Gly Ala Val Thr Ala
    50                  55                  60

Asp Asn Pro Lys Asn Glu Asp Glu Val Ala Gln Asn Asp Met Pro Gln
65                  70                  75                  80
```

```
Asn Ala Ala Gly Thr Asp Ser Ser Thr Pro Asn His Thr Pro Asp Pro
                85                  90                  95

Asn Met Leu Ala Gly Asn Met Glu Asn Gln Ala Thr Asp Ala Gly Glu
            100                 105                 110

Ser Ser Gln Pro Ala Asn Gln Pro Asp Met Ala Asn Ala Ala Asp Gly
        115                 120                 125

Met Gln Gly Asp Asp Pro Ser Ala Gly Gln Asn Ala Gly Asn Thr
    130                 135                 140

Ala Ala Gln Gly Ala Asn Gln Ala Gly Asn Asn Gln Ala Ala Gly Ser
145                 150                 155                 160

Ser Asp Pro Ile Pro Ala Ser Asn Pro Ala Pro Ala Asn Gly Gly Ser
                165                 170                 175

Asn Phe Gly Arg Val Asp Leu Ala Asn Gly Val Leu Ile Asp Gly Pro
            180                 185                 190

Ser Gln Asn Ile Thr Leu Thr His Cys Lys Gly Asp Ser Cys Ser Gly
        195                 200                 205

Asn Asn Phe Leu Asp Glu Glu Val Gln Leu Lys Ser Glu Phe Glu Lys
    210                 215                 220

Leu Ser Asp Ala Asp Lys Ile Ser Asn Tyr Lys Lys Asp Gly Lys Asn
225                 230                 235                 240

Asp Lys Phe Val Gly Leu Val Ala Asp Ser Val Gln Met Lys Gly Ile
                245                 250                 255

Asn Gln Tyr Ile Ile Phe Tyr Lys Pro Lys Pro Thr Ser Phe Ala Arg
            260                 265                 270

Phe Arg Arg Ser Ala Arg Ser Arg Arg Ser Leu Pro Ala Glu Met Pro
        275                 280                 285

Leu Ile Pro Val Asn Gln Ala Asp Thr Leu Ile Val Asp Gly Glu Ala
    290                 295                 300

Val Ser Leu Thr Gly His Ser Gly Asn Ile Phe Ala Pro Glu Gly Asn
305                 310                 315                 320

Tyr Arg Tyr Leu Thr Tyr Gly Ala Glu Lys Leu Pro Gly Gly Ser Tyr
                325                 330                 335

Ala Leu Arg Val Gln Gly Glu Pro Ala Lys Gly Glu Met Leu Ala Gly
            340                 345                 350

Ala Ala Val Tyr Asn Gly Glu Val Leu His Phe His Thr Glu Asn Gly
        355                 360                 365

Arg Pro Tyr Pro Thr Arg Gly Arg Phe Ala Ala Lys Val Asp Phe Gly
    370                 375                 380

Ser Lys Ser Val Asp Gly Ile Ile Asp Ser Gly Asp Asp Leu His Met
385                 390                 395                 400

Gly Thr Gln Lys Phe Lys Ala Ala Ile Asp Gly Asn Gly Phe Lys Gly
                405                 410                 415

Thr Trp Thr Glu Asn Gly Ser Gly Asp Val Ser Gly Lys Phe Tyr Gly
            420                 425                 430

Pro Ala Gly Glu Glu Val Ala Gly Lys Tyr Ser Tyr Arg Pro Thr Asp
        435                 440                 445

Ala Glu Lys Gly Gly Phe Gly Val Phe Ala Gly Lys Lys Glu Gln Asp
    450                 455                 460

<210> SEQ ID NO 7
<211> LENGTH: 644
<212> TYPE: PRT
<213> ORGANISM: N. meningitidis
```

```
<400> SEQUENCE: 7

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
                20                  25                  30

Gln Ala Gly Ser Gln Gly Gln Gly Ala Pro Ser Ala Gln Gly Gly Gln
            35                  40                  45

Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Pro Ser Ala Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Glu Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415
```

Gly Asn Gly Phe Lys Gly Thr Trp Thr Glu Asn Gly Gly Asp Val
            420                 425                 430

Ser Gly Lys Phe Tyr Gly Pro Ala Gly Glu Val Ala Gly Lys Tyr
            435                 440                 445

Ser Tyr Arg Pro Thr Asp Ala Glu Lys Gly Phe Gly Val Phe Ala
        450                 455                 460

Gly Lys Lys Glu Gln Asp Gly Ser Gly Gly Gly Ala Thr Tyr Lys
465                 470                 475                 480

Val Asp Glu Tyr His Ala Asn Ala Arg Phe Ala Ile Asp His Phe Asn
                485                 490                 495

Thr Ser Thr Asn Val Gly Gly Phe Tyr Gly Leu Thr Gly Ser Val Glu
            500                 505                 510

Phe Asp Gln Ala Lys Arg Asp Gly Lys Ile Asp Ile Thr Ile Pro Val
            515                 520                 525

Ala Asn Leu Gln Ser Gly Ser Gln His Phe Thr Asp His Leu Lys Ser
530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
            580                 585                 590

Phe Asn Cys Tyr Gln Ser Pro Met Ala Lys Thr Glu Val Cys Gly Gly
                595                 600                 605

Asp Phe Ser Thr Thr Ile Asp Arg Thr Lys Trp Gly Val Asp Tyr Leu
        610                 615                 620

Val Asn Val Gly Met Thr Lys Ser Val Arg Ile Asp Ile Gln Ile Glu
625                 630                 635                 640

Ala Ala Lys Gln

<210> SEQ ID NO 8
<211> LENGTH: 434
<212> TYPE: PRT
<213> ORGANISM: N. meningitidis

<400> SEQUENCE: 8

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asn Arg His
    50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Glu Gly Val Tyr Asn Tyr
                85                  90                  95

Ile Thr Val Ala Ser Leu Pro Arg Thr Ala Gly Asp Ile Ala Gly Asp
            100                 105                 110

Thr Trp Asn Thr Ser Lys Val Arg Ala Thr Leu Leu Gly Ile Ser Pro
        115                 120                 125

Ala Thr Gln Ala Arg Val Lys Ile Val Thr Tyr Gly Asn Val Thr Tyr
130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
            165                 170                 175

Tyr Val Gln Arg Gly Ser Gly Gly Gly Val Ala Ala Asp Ile Gly
            180                 185                 190

Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
            210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
            245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
            275                 280                 285

Gln Thr Glu Gln Ile Gln Asp Ser Glu His Ser Gly Lys Met Val Ala
            290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
            325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
            355                 360                 365

Asn Val Asp Leu Ala Ala Ala Asp Ile Lys Pro Asp Gly Lys Arg His
            370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
            405                 410                 415

Ala Glu Val Lys Thr Val Asn Gly Ile Arg His Ile Gly Leu Ala Ala
            420                 425                 430

Lys Gln

<210> SEQ ID NO 9
<211> LENGTH: 6
<212> TYPE: PRT
<213> ORGANISM: Artificial Sequence
<220> FEATURE:
<223> OTHER INFORMATION: Linker sequence

<400> SEQUENCE: 9

Gly Ser Gly Gly Gly Gly
1               5

<210> SEQ ID NO 10
<211> LENGTH: 255
<212> TYPE: PRT
<213> ORGANISM: N. meningitidis

```
<400> SEQUENCE: 10

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 11
<211> LENGTH: 254
<212> TYPE: PRT
<213> ORGANISM: N. meningitidis

<400> SEQUENCE: 11

Cys Ser Ser Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110
```

```
Lys Ile Asn Asn Pro Asp Lys Ile Asp Ser Leu Ile Asn Gln Arg Ser
            115                 120                 125

Phe Leu Val Ser Gly Leu Gly Gly Glu His Thr Ala Phe Asn Gln Leu
        130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 12
<211> LENGTH: 262
<212> TYPE: PRT
<213> ORGANISM: N. meningitidis

<400> SEQUENCE: 12

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asn His Ser
            100                 105                 110

Ala Val Val Ala Leu Gln Ile Glu Lys Ile Asn Asn Pro Asp Lys Thr
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Pro Asn Gly Arg Leu His Tyr Ser
                165                 170                 175

Ile Asp Phe Thr Lys Lys Gln Gly Tyr Gly Arg Ile Glu His Leu Lys
            180                 185                 190

Thr Leu Glu Gln Asn Val Glu Leu Ala Ala Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240
```

```
Ile Ala Gly Ser Ala Thr Val Lys Ile Gly Glu Lys Val His Glu Ile
            245                 250                 255

Gly Ile Ala Gly Lys Gln
            260
```